United States Patent [19]

Ohashi et al.

[11] Patent Number: 5,648,359
[45] Date of Patent: Jul. 15, 1997

[54] TUMOR NECROSIS FACTOR PRODUCTION INHIBITORS

[75] Inventors: Naohito Ohashi, Takatsuki; Norio Fujiwara, Toyonaka, both of Japan; Yutaka Ueda, Brookline, Mass.

[73] Assignee: Sumitomo Pharmaceuticals Company, Limited, Osaka, Japan

[21] Appl. No.: 365,427

[22] Filed: Dec. 28, 1994

[30] Foreign Application Priority Data

Dec. 28, 1993 [JP] Japan ..................... 5-350037

[51] Int. Cl.$^6$ .................. A61K 31/44; A61K 31/445; C07D 491/153; C07D 491/18
[52] U.S. Cl. ................ 514/279; 514/281; 546/39; 546/44; 546/45
[58] Field of Search ................ 546/44, 39, 45; 514/281, 279

[56] References Cited

PUBLICATIONS

Acta Universitatis Palackianae Olomucenis, vol. 90, pp. 5–14, (1979); Maturovam et al.
Katzung, Basic and Clinical Pharmacology, Sixth Edition, pp. 871–872 Prentice Hall pub. (1995).
Collection Czechoslovak Chem. Commun. 52(9), 2338–2346 (1987); Hana Paulova et al.
J. Pharm. Pharmacol. 45(8), 707–710 (1993); Feng–Nien Ko et al.
Pharmocology Biochemistry & Behavior, 20(3),355–360 (1984); Gerhard Meisenberg et al.
Kaohsiung J. Med. Sci., 5, 132–145 (1989); Ian–Lih Tsai et al.
Canadian Journal of Chemistry, 43, 2180–2182 (1965); Richard H.F. Manske et al.
Canadian Journal of Chemistry, 43, 2183–2189 (1965); Richard H.F. Manske et al.
Collection Czechoslovak Chem. Commun., 51(8), 1743–1751 (1986); Jiri Slavik et al.
Journal of Natural Products, 51(4), 760–764 (1988); Belkis Gozler et al.
Journal of Natural Products, 53(5) 1267–1271 (1990); Shoe–i–Sheng Lee et al.
Journal of Chromatography, 587(2), 314–317 (1991); Jean–Pierre Rey et al.
Chromatographia,, 37, 579–583 (1993); H. Stuppner et al.
J. Chem. Soc. (C), 1317–1323 (1967); A.C. Barker et al.
Journal of the Taiwan Pharmaceutical Association, 28, 43–55 (1976); Chung–hsiung Chen et al.

*Primary Examiner*—Alan L. Rotman
*Attorney, Agent, or Firm*—Sughrue, Mion, Zinn, Macpeak & Seas

[57] ABSTRACT

There is provided a composition for inhibiting the production or secretion of tumor necrosis factor effective for the treatment of cachexia, septic shock, multiple organ failure, rheumatoid arthritis, inflammatory bowel disease, multiple sclerosis, osteoarthritis, Behcet disease, systemic lupus erythematosus (SLE), graft versus host disease (GvHD), malaria, acquired immune deficiency syndrome (AIDS), meningitis, hepatitis and Type II diabetes mellitus. The composition comprises a pharmaceutically effective amount of a compound of formula (1).

21 Claims, No Drawings

TUMOR NECROSIS FACTOR PRODUCTION INHIBITORS

BACKGROUND OF THE INVENTION

1. Field of the Invention

The present invention relates to a new medical use of a compound for inhibiting the production or secretion of a tumor necrosis factor.

2. Related Art

A tumor necrosis factor (hereinafter abbreviated as TNF) is a peptide of 157 amino acids, having a molecular weight of about 17,000. TNF is one of cytokines produced by various cells including macrophages.

TNF had been firstly found out as a cytokine showing a cytotoxic effect on tumor. The recent studies have revealed that the activities of TNF are not only limited to tumor cells but also extended to many other normal cells. Examples of such TNF activities include suppression of the lipoprotein lipase activity in adipocytes, expression of HLA antigen on blood endothelial cells and fibroblasts, interleukin-1 production by fibroblasts or macrophages, activation of cytotoxic macrophages, suppression of CFU, production of colony stimulating factor by fibroblasts, endothelial cells or some tumor cells, inhibition of the synthesis of proteoglycans and stimulation of their resorption in cartilage, activation of neutrophils and generation of superoxide, production of procoagulant factor by blood endothelial cells, proliferation of fibroblasts, change in membrane potential of skeletal muscle, interferon $\beta_2$ production by fibroblasts, and injury of blood endothelial cells. In these days, TNF has thus been recognized to be a cytokine which takes part broadly in vital protection through inflammation and immune response [Vassalli, P., Ann. Rev. Immunol., 10, 411–452 (1992)].

On the other hand, it is noted that continuous or excessive production of TNF rather results in vigorous actions on normal cells to cause various diseases. For example, TNF is also known as cachectin which induces cachexia in cancer or infectious diseases, involving catabolic acceleration of total metabolism to cause extreme wasting [B. Beutler, D. Greenwald, J. D. Hulmes et al., Nature, 316, 552–554 (1985), Kawakami, M., SEIKAGAKU (Biochemistry), 59, 1244–1247 (1987)].

TNF is one of causes for a septic shock; in an experiment using an antibody, its effect has been recognized [Starnes, H. F. Jr., Pearce, M. K., Tewari, A., Yim, J. H., Zou, J. C., Abrams, J. S., J. Immunol., 145, 4185–4191 (1990), Beutler, B., Milsark, I. W., Cerami, A. C., Science, 229, 869–871 (1985), Hinshaw, L. B., Tekamp-Olson, P., Chang, A. C. K. et al., Circ. Shock, 30, 279–292 (1990)].

An increased level of TNF is also observed in the synovial fluid or blood from patients with rheumatoid arthritis [Tetta, C., Camussi, G., Modena, V., Vittorio, C. D., Baglioni, C., Ann. Rheum. Dis., 49, 665–667 (1990)].

In addition, there are many other diseases of which a certain role of TNF is suspected, e.g., osteoarthritis reported by Venn, G., Nietfeld, J. J., Duits, A. J., Brennan, F. M., Arner, E., Covington, M., Billingham, M. E. J., Hardingham, T. E., Arthritis Rheum., 36 (6), 819–826 (1993); multiple sclerosis reported by Sharief, M. K., Hentges, R., N. Engl. J. Med., 325 (7), 467–472 (1991); Kawasaki disease reported by Matsubara, T., Furukawa, S., Yabuta, K., Clin. Immunol. Immunopathol., 56, 29–36 (1990); inflammatory bowel disease such as ulcerative colitis or Crohn's disease reported by Murch, S., Walker-Smith, J. A., Arch. Dis. Child, 66, 561 (1991); Maeda, M., SHOKAKI-TOMENEKI (Digestive Organ and Immunity), 22, 111–114 (1989), Behcet disease reported by Akoglu, T., Direskeneli, H., Yazici, H., Lawrence, R., J. Rheumatol., 17, 1107–1108 (1990); systemic lupus erythematosus (SLE) reported by Maury, C. P. J., Teppo, A.-M., Arthritis Rheum., 32, 146–150 (1989); graft versus host disease (GvHD) reported by Nestel, F. P., Price, K. S., Seemayer, T. A., Lapp, W. S., J. Exp. Med., 175, 405–413 (1992); multiple organ failure reported by Fujiwara, T., Kawakami, M., RINSHO-I (Clinician), 17 (10), 2006–2008 (1991); malaria reported by Grau, G. E., Fajardo, L. F., Piguet, P. F. et al., Science, 237, 1210–1212 (1987), acquired immune deficiency syndrome (AIDS) reported by Kawakami, M., Hayata K., Medical Immunology, 20, 615–620 (1990), Dezube, B. J., Pardee, A. B., J. Acquir. Immune Defic. Syndr., 5, 1099–1104 (1992); meningitis reported by Waage, A., Halstensen, A., Espevik, T., Lancet, I, 355–357 (1987); hepatitis reported by Sugano, K., KANZO (Liver), 33, 213–218 (1992), Type II diabetes mellitus reported by Hotamisligil, G. S., Shargill, N. S., Spiegelman, B. M., Science, 259, 87–91 (1993), etc.

From the above publications, it is understood that excessive production of TNF sometimes adversely affect the living body. Therefore, further investigations are desired to develop TNF inhibitors available for the treatment of these diseases.

Pentoxifylline having a methylxanthine skeleton is known as a compound showing an activity of inhibiting TNF. It is reported that this compound possesses an activity of preventing death in endotoxin-shocked mice, an activity of improving the sense of well-being or preventing a weight loss in cancer patients, an activity of preventing experimental allergic encephalomyelitis induced on an animal model, and an activity of preventing HIV-1 replication, reported by Zabel, P., Schade, F. U., Schlaak, M., Immunobiol., 187, 447–463 (1993), Dezube, B. J., Pardee, A. B. et al., Cancer Immuno. Immunother., 36, 57–60 (1993), Nataf, S., Louboutin, J. P., Chabannes, D., Fève, J. R., Muller, J. Y., Acta Neurol. Scand., 38, 97–99 (1993), Fazely, F., Dezube, B. J., Allen-Ryan, J., Pardee, A. B., Ruprecht, R. M., Blood, 77, 1653–1656 (1991). In addition, glucocorticoid, protease inhibitors, phospholipase $A_2$ inhibitors, lipoxygenase inhibitors, platelet-aggregating factor (PAF) antagonists, radical scavengers, prostaglandin $F_2$ or $I_2$ and anti-TNF antibody are heretofore known as compounds or factors for showing a TNF inhibitory activity.

In the future, the role of TNF in association with diseases will be made clearer, using these low molecular compounds or antibodies. However, these compounds are accompanied by side effects due to a wide variety of the pharmacological activities. Therefore, it is desired to develop highly safe compounds based on a novel mechanism.

As a compound which is one of the effective ingredients of the composition of the present invention and has a structure close to the compounds of the present invention, there is known a compound named Eschscholtzine or crychine. The compound has the following structure:

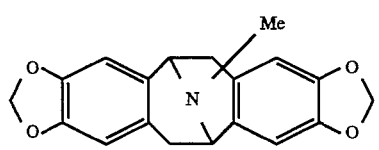

Eschscholtzine is a natural substance isolated from a plant (Manske, R. H. F., Shin, K. H., Can. J. Chem., 43 (8), 2180–2182 (1965), Manske, R. H. F., Shin, K. H., Battersby, A. R., Shaw, D. F., Can. J. Chem., 43 (8), 2183–2189 (1965)). This substance is also synthesized by Barker, A. C., Battersby, A. R., J. Chem. Soc. (C), 1317–1323 (1967). It is reported that the compound has a pharmacological activity as a vasorelaxant (Ko, F.N., Wo, Y. C., Lu, S.T., Teng, C. M., J. Pharm. Pharmacol., 45 (8), 707–710 (1993)). However, no report is found on the activity of inhibiting the production or secretion of TNF as contemplated by the present invention.

SUMMARY OF THE INVENTION

The present invention provides a pharmaceutical composition for the treatment of diseases, based on the activity of inhibiting the production or secretion of TNF, in which TNF is considered to take a part, for example, in cachexia, septic shock, multiple organ failure, Rhuematoid arthritis, inflammatory bowel disease, multiple sclerosis, osteoarthritis Behcet disease, systemic lupus erythematosus (SLE), graft versus host disease (GvHD), malaria, acquired immune deficiency syndrome (AIDS), meningitis, hepatitis, or Type II diabetes mellitus.

The present inventors have discovered that the compounds represented by general formula (1) described below exhibit an activity of inhibiting the production or secretion of TNF. The present invention has thus been accomplished.

That is, a first aspect of the present invention relates to a method for preventing or treating a disease caused by TNF, which comprises administering to a patient a pharmaceutically effective amount of a compound represented by general formula (1) below:

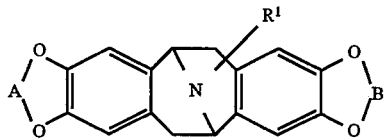

(1)

wherein $R^1$ represents a hydrogen atom, an alkyl group, an alkenyl group, an acyl group or a group shown by formula:

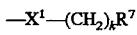

—$X^1$—$(CH_2)_kR^7$ wherein $R^7$ represents a halogen atom, a hydroxyl group, an alkoxy group, an alkylthio group, a carboxyl group, an alkoxycarbonyl group, an aryloxycarbonyl group, a cyano group, an amino group, an alkylamino group, a dialkylamino group, a cycloalkyl group, a heterocyclic group, an aromatic hydrocarbon group or an aromatic heterocyclic group; $X^1$ represents a carbonyl group or a methylene group; k represents 0 or an integer of 1 to 5, provided that when $X^1$ is a carbonyl group and $R^7$ is a hydroxyl group, or when $X^1$ is a methylene group and $R^7$ is a hydroxyl group, an amino group, an alkylamino group or a dialkylamino group, k represents an integer of 1 to 5;

and, each of A and B independently represents a methylene group or a group shown by:

(2)

wherein each of $R^2$ and $R^3$ independently represents a hydrogen atom, an alkyl group, an alkoxycarbonyl group or a substituted alkyl group; or a pharmaceutically acceptable salt thereof.

A second aspect of the present invention relates to use of the above compound represented by formula (1) for the preparation of a pharmaceutical composition for preventing or treating a disease caused by TNF.

A third aspect of the present invention relates to a new compound represented by general formula:

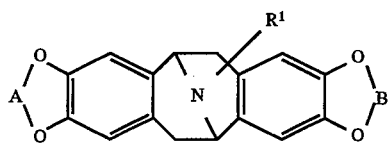

wherein $R^1$, A and B are as defined above, provided that when $R^1$ is methyl, A and B are not methylene simultaneously; or a salt thereof.

A fourth aspect of the present invention relates to a pharmaceutical composition for inhibiting the preparation or secretion of TNF, which comprises as an effective ingredient a pharmaceutically effective amount of the above new compound or a pharmaceutically acceptable salt thereof and a pharmaceutically acceptable carrier or diluent.

A fifth aspect of the present invention relates to the above new compound for use as a medicament.

DETAILED DESCRIPTIONS OF THE INVENTION

The functional groups in the compounds given above are described below in more detail.

In the compounds of the present invention, k represents 0 or an integer of 1 to 5 when $R^1$ is shown by the formula: —$X^1$—$(CH_2)_kR^7$. Compounds of general formula (1) wherein k is 0, 1 or 2 are preferred for the present invention.

As the alkyl group and the alkenyl group, a lower alkyl group and a lower alkenyl group are preferred, respectively. As the acyl group, preferred are a lower alkanoyl group and an aroyl group having carbon atoms of 11 or less, e.g., a benzoyl group. A preferred example of the alkoxy group is a lower alkoxy group. As the alkylthio group, the alkoxycarbonyl group, the alkylamino group, the dialkylamino group and the cycloalkyl group, preferred are a lower alkylthio group, a lower alkoxycarbonyl group, a lower alkylamino group, a lower dialkylamino group and a lower cycloalkyl group, respectively.

The lower alkyl group includes a straight or branched alkyl group having 1 to 6 carbon atoms. Specific examples of the lower alkyl group include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl and 1,1,2-trimethylpropyl. The alkyl groups having 1 to 3 carbon atoms are preferred.

The lower alkenyl group includes a straight or branched alkenyl group having 2 to 6 carbon atoms. Specific examples of the lower alkenyl group include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and 3-methyl-2-butenyl. Preferred alkenyl group have 2 to 3 carbon atoms.

The lower alkanoyl group includes a straight or branched alkanoyl group having 1 to 6 carbon atoms. Specific examples of the lower alkanoyl group include formyl, acetyl, propionyl, butyryl, valeryl, isovaleryl, pivaloyl and hexanoyl.

Examples of the halogen atom include fluorine, chlorine, bromine and iodine.

The lower alkoxy group includes a straight or branched alkoxy group having 1 to 6 carbon atoms. Specific examples of the lower alkoxy group include methoxy, ethoxy, propoxy, 1-methylethoxy, butoxy, 1-methylpropoxy, 2-methylpropoxy, pentyloxy, 1-methylbutoxy, 2-methylbutoxy, 3-methylbutoxy, 1,1-dimethylpropoxy, 1,2-dimethylpropoxy, 2,2-dimethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethyl-1-methylpropoxy and 1-ethyl-2-methylpropoxy.

The lower alkylthio group includes a straight or branched alkylthio group having 1 to 6 carbon atoms. Specific examples of the lower alkylthio group include methylthio, ethylthio, propylthio, 1-methylethylthio, butylthio, 1-methylpropylthio, 2-methylpropylthio, pentylthio, 1-methylbutylthio, 2-methylbutylthio, 3-methylbutylthio, 1,1-dimethylpropylthio, 1,2-dimethylpropylthio, 2,2-dimethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethyl-1-methylpropylthio and 1-ethyl-2-methylpropylthio.

The lower alkoxycarbonyl group includes a straight or branched alkoxycarbonyl group having 2 to 6 carbon atoms. Specific examples of the lower alkoxycarbonyl group include methoxycarbonyl, ethoxycarbonyl, propoxycarbonyl, 1-methylethoxycarbonyl, butoxycarbonyl and 1,1-dimethylethoxycarbonyl.

The aryloxycarbonyl group has preferably 7 to 13 carbon atoms. A specific example is phenoxycarbonyl.

The lower alkylamino group includes an alkylamino group having 1 to 4 carbon atoms and specific examples include methylamino, ethylamino, propylamino, 1-methylethylamino, butylamino and 1,1-dimethylethylamino.

The di-lower alkylamino group includes a dialkylamino group having 2 to 8 carbon atoms and specific examples thereof include N,N-dimethylamino, N,N-diethylamino, N,N-dipropylamino, N-methyl-N-ethylamino, N,N-dibutylamino and N-methyl-N-(1,1-dimethylethyl)amino.

The lower cycloalkyl group includes a cycloalkyl group having 3 to 7 carbon atoms and specific examples include cyclopropyl, cyclobutyl, cyclopentyl and cyclohexyl.

The heterocyclic group includes a monocyclic heterocyclic group which is saturated, has carbon atoms of 6 or less and contains as a hetero atom(s) one or two nitrogen, oxygen or sulfur atom(s) which may be the same or different. More preferably, the monocyclic heterocyclic group is selected from 5- and 6-membered heterocyclic groups. Specific examples of the 5-membered heterocyclic group include 1-pyrrolidinyl, 2-pyrrolidinyl, 3-pyrrolidinyl, 2-oxolanyl, 3-oxolanyl, 2-thiolanyl and 3-thiolanyl. Specific examples of the 6-membered heterocyclic group include piperidino, 2-piperidyl, 3-piperidyl, 4-piperidyl, 1-piperazinyl, 2-piperazinyl, 2-tetrahydropyranyl, 3-tetrahydropyranyl, 4-tetrahydropyranyl, morpholino, 2-morpholinyl and 3-morpholinyl.

The monocyclic heterocyclic group may be optionally substituted with an alkyl group.

The aromatic hydrocarbon group has preferably carbon atoms of 10 or less and specific examples are phenyl, 1-naphthyl and 2-naphthyl.

The aromatic hydrocarbon group may be optionally substituted with, e.g., a halogen atom, a hydroxyl group, an alkyl group, an alkoxy group, a nitro group or a cyano group.

The aromatic heterocyclic group includes a monocyclic aromatic heterocyclic group having carbon atoms of 5 or less which contains as a hetero atom(s), which may be the same or different, 1 to 3 nitrogen, oxygen or sulfur atoms. Specific examples of the aromatic heterocyclic group include 2-pyridyl, 3-pyridyl, 4-pyridyl, 2-pyrimidinyl, 4-pyrimidinyl, 5-pyrimidinyl, 2-thiazolyl, 4-thiazolyl, 5-thiazolyl, 2-oxazolyl, 4-oxazolyl, 5-oxazolyl, 3-isoxazolyl, 4-isoxazolyl, 5-isoxazolyl, 3-isothiazolyl, 4-isothiazolyl, 5-isothiazolyl, 2-furyl, 3-furyl, 2-imidazolyl, 4-imidazolyl, 2-thienyl, 3-thienyl, 2-pyrrolyl, 3-pyrrolyl, 1-pyrazolyl, 3-pyrazolyl, 4-pyrazolyl, 2-pyrazinyl, 3-pyridazinyl, 4-pyridazinyl, 1H-1,2,4-triazol-1-yl, 1H-1,2,4-triazol-3-yl, 1H-1,2,4-triazol-5-yl, 3-oxadiazolyl, 5-oxadiazolyl, 2-thiazolyl, 4-thiazolyl and 5-thiazolyl.

As the substituted alkyl group, there are, e.g., a substituted lower alkyl group having 1 to 3 carbon atoms of the alkyl moiety, which is substituted with, e.g., a hydroxyl group, an amino group, an alkylamino group or a dialkylamino group. Herein the alkylamino group and the dialkylamino group are preferably a lower alkylamino group and a di-lower alkylamino group, respectively. These groups may also be substituted with a hydroxyl group, an amino group, an alkylamino group or a dialkylamino group. Specific examples of the substituted alkyl group include hydroxymethyl, aminomethyl, N-methylaminomethyl, N,N-dimethylaminomethyl, N-(2-hydroxyethyl)aminomethyl and N-[2-(N,N-dimethylamino)ethyl]aminomethyl.

Typical examples of the salts which are also covered by the present invention include salts with mineral acids such as hydrochloric acid, hydrobromic acid, sulfuric acid or phosphoric acid; salts with organic carboxylic acids such as formic acid, acetic acid, fumaric acid, maleic acid, malic acid, tartaric acid, aspartic acid or glutamic acid; salts with sulfonic acids such as methanesulfonic acid, benzenesulfonic acid, p-toluenesulfonic acid, hydroxybenzenesulfonic acid or dihydroxybenzenesulfonic acid; salts with alkali metals such as sodium or potassium; salts with alkaline earth metals such as calcium or magnesium; salts with organic bases such as trimethylamine, triethylamine or pyridine, or ammonium salts.

The compounds of the present invention include stereoisomers and geometrical isomers. The compounds of the present invention also include all of the hydrates and crystalline forms.

The composition of the present invention for inhibiting the production or secretion of TNF may be administered orally or parenterally. More specifically, the composition may be administered orally in a conventional form, e.g., in the form of tablets, capsules, syrup or suspension. The composition in a liquid form such as a solution, an emulsion or a suspension may be parenterally administered in the form of injection. The composition may also be administered rectally in the form of a suppository. These pharmaceutical preparations can be prepared in a conventional manner by formulating the active ingredient together with a conventional carrier, excipient, binder, stabilizer, etc. Where the pharmaceutical composition is provided in the form of injection, a buffering agent, a dissolution aid, an isotonic agent or the like may also be added to the composition.

Dose of the TNF inhibitor and the time for administration vary depending upon conditions, age, body weight and preparation form. In general, the daily dose of the TNF inhibitor for adult is in the range of 10 to 500 mg for oral administration and, for parenteral administration in the range of 1 to 100 mg. The composition is administered at the daily dose at once or by dividing the daily dose into several times.

The compounds of the present invention can be synthesized, e.g., by the following processes.

Process 1

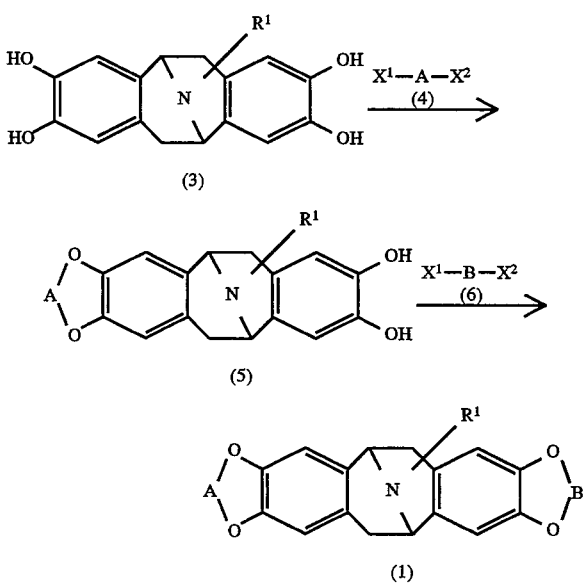

wherein $R^1$, A and B are as defined above; and each of $X^1$ and $X^2$ independently represents a halogen atom such as chlorine, bromine or iodine.

The compound shown by general formula (1) can be prepared by reacting a dicatechol compound shown by general formula (3) with a dihalide shown by general formula (4) in an inert solvent in the presence of a base and then reacting the resulting monocatechol compound represented by general formula (5) with a dihalide of general formula (6) in the presence of a base.

The solvent used in the above reaction is typically an aprotic solvent, for example, N,N-dimethylformamide, dimethylsulfoxide, hexamethylphosphoramide or acetonitrile.

As the base, there are inorganic bases such as potassium carbonate, cesium carbonate, potassium fluoride, cesium fluoride, sodium hydroxide, and sodium hydride.

In the reaction described above, a proportion of the catechol derivatives (3) or (5) to the dihalides (4) or (6) is not particularly limited. In general, the dihalides are appropriately used between the equimolar amount and the amount more than the equimolar amount, based on the catechol derivatives. The reactants are used preferably in an almost equimolar amount. The base is used in an amount more than the equimolar amount to the dihalides. The reaction is carried out generally at a temperature ranging from ice cooling to about 150° C.

Where A and B represent the same group in general formula (1), the reaction is carried out in the presence of a base, using more than 2 mols of the dihalide (4), based on the compound of general formula (3). The compound of general formula (5) can be led to the compound of general formula (1), without isolating the compound (5).

Process 2

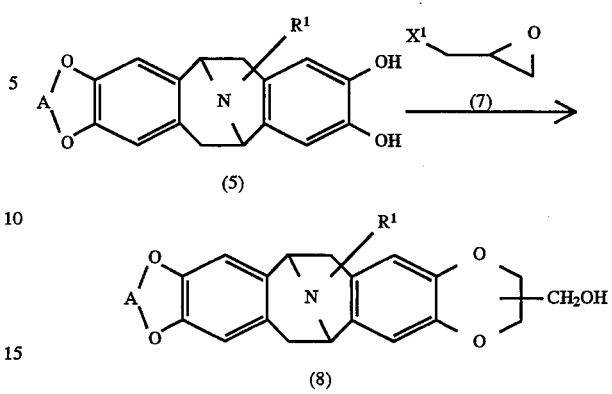

wherein A, $R^1$ and $X^1$ are as defined above.

The compound represented by general formula (8) which corresponds to the compound of general formula (1), wherein substituent B is ethylenedioxy substituted with hydroxymethyl, can be prepared, e.g., by the following process.

The compound shown by general formula (8) can be prepared by reacting the monocatechol compound shown by general formula (5) with an epihalohydrin shown by general formula (7) in an inert solvent in the presence of a base. The solvent, base, reaction temperature and other reaction conditions used are similar to those for Process 1 described above.

Process 3

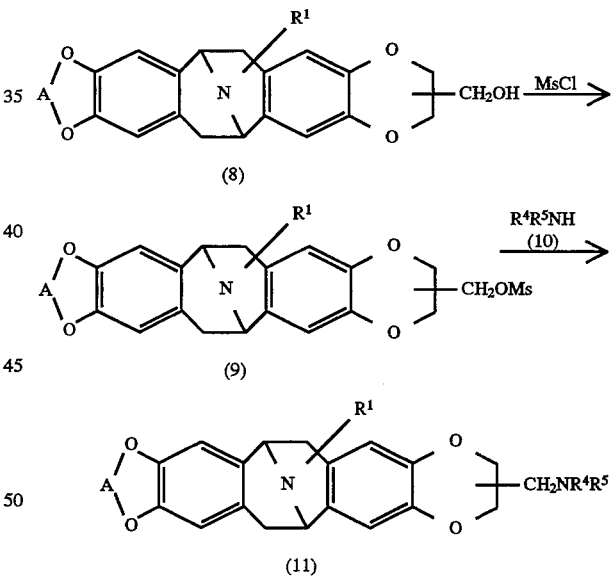

wherein $R^1$ and A are as defined above; and each of $R^4$ and $R^5$ independently represents a hydrogen atom, an alkyl group or a substituted alkyl group.

The compound represented by general formula (11) which corresponds to the compound of general formula (1), wherein substituent B is an ethylenedioxy group having a substituted aminomethyl, can be prepared, e.g., by the following process.

The compound shown by general formula (11) can be prepared by reacting a hydroxy compound shown by general formula (8) with methanesulfonyl chloride in an inert solvent in the presence of a base and then reacting the resulting compound represented by general formula (9) with an amine represented by general formula (10).

Examples of the solvent used in the synthesis of the compound (9) are aprotic polar solvents such as N,N-dimethylformamide, dimethylsulfoxide, hexamethylphosphoramide, and acetonitrile; hydrocarbons such as benzene, toluene or hexane; halogenated hydrocarbons such as dichloromethane, chloroform or dichloroethane; and ethers such as tetrahydrofuran, dioxane or diethyl ether.

Examples of the base include organic tertiary amines such as triethylamine, pyridine, N,N-dimethylaminopyridine, and N-methylmorpholine.

In the reaction above, a proportion of methanesulfonyl chloride to the hydroxy compound represented by general formula (8) is not particularly limited but appropriately chosen between the equimolar amount and the amount more than the equimolar amount, based on to the hydroxy compound. Preferably, the reactants are used in an almost equimolar amount.

The base is employed in an amount more than the equimolar amount, based on methanesulfonyl chloride. The reaction is carried out at a temperature ranging from ice cooling to about room temperature.

Examples of the solvent, which is used in the synthesis of the compound shown by general formula (11) from the compound of general formula (9), are aprotic polar solvents such as N,N-dimethylformamide, dimethylsulfoxide, hexamethylphosphoramide or acetonitrile; halogenated hydrocarbons such as dichloromethane, chloroform, or dichloroethane; and ethers such as tetrahydrofuran, dioxane or diethyl ether.

In the reaction described above, the amine derivative of formula (10) is used in an excess amount based on the compound of formula (9). The reaction is carried out generally at a temperature ranging from ice cooling to about 150° C.

Processes 1 to 3 are directed to the conversion of the compounds having the substituted amino group in the catechol moiety thereof. In addition to these processes, the compounds of general formula (1) may also be prepared through conversion at the catechol moiety followed by introduction of a substituent at the amino group.

Process 4

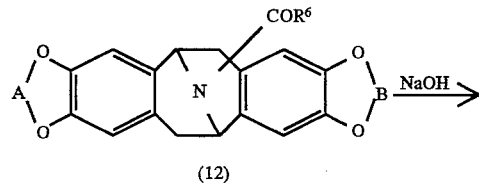

(12)

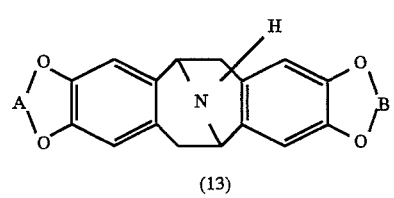

(13)

wherein A and B are as defined above, and $R^6$ represents an alkyl group.

The compound represented by general formula (13) corresponding to the compound of general formula (1), wherein substituent $R^1$ is a hydrogen atom, can be prepared by hydrolysis of an acyl derivative represented by general formula (12).

The hydrolysis may proceed in a solvent mixture of a potassium hydroxide or sodium hydroxide aqueous solution with an alcoholic solvent such as ethanol, ethylene glycol or methoxyethanol, or with an ether such as 1,4-dioxane or tetrahydrofuran, at a temperature ranging from room temperature to the boiling point of the solvent used.

Process 5

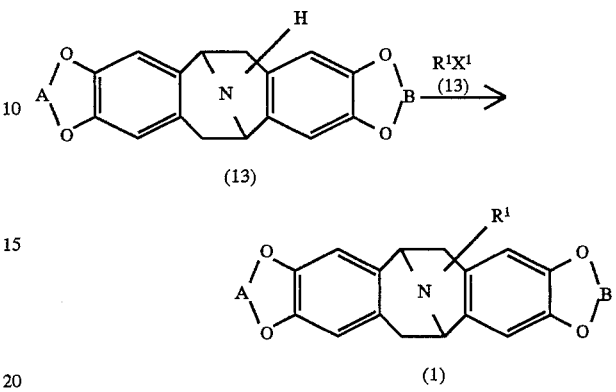

(13)

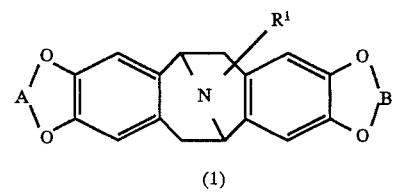

(1)

wherein $R^1$, A, B and $X^1$ are as defined above.

The compound represented by general formula (1) can be prepared, e.g., by reacting an amino derivative shown by general formula (13) with a halide shown by general formula (14) in an inert solvent in the presence of a base.

Examples of the solvent used are aprotic polar solvents such as N,N-dimethylformamide, dimethylsulfoxide, hexamethylphosphoramide or acetonitrile; hydrocarbons such as benzene, toluene or hexane; halogenated hydrocarbons such as dichloromethane, chloroform or dichloroethane; and ethers such as tetrahydrofuran, dioxane or diethyl ether.

Examples of the base include organic tertiary amines such as triethylamine, pyridine, N,N-dimethylaminopyridine or N-methylmorpholine; and inorganic bases such as potassium carbonate, sodium carbonate or sodium hydrogencarbonate.

In the reaction above, a proportion of the amino derivative to the halide of formula (14) is not particularly limited. In general, the halide (14) may be used in an amount more than the equimolar amount based on the amino derivative. Preferably, the reactants are used in an almost equimolar amount. The base is employed in an amount more than the equimolar amount based on the halide. The reaction is carried out at a temperature ranging from ice cooling to about the boiling point of the solvent used.

Process 6

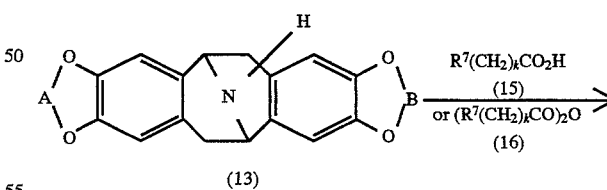

(13)

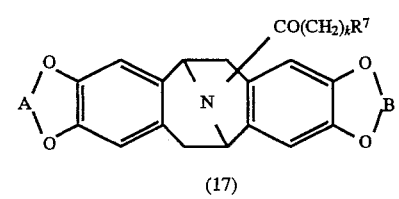

(17)

wherein A, B, k and $R^7$ are as defined above.

The compound represented by general formula (17) corresponding to the compound of general formula (1), wherein substituent $R^1$ is a group represented by formula —CO $(CH_2)_kR^7$, can also be prepared either by condensing the amine derivative represented by general formula (13) with the carboxylic acid represented by general formula (15), or by reacting the amine derivative (13) with an acid anhydride shown by general formula (16) in the presence of a base, in an inert solvent.

Examples of the condensing agent used in the condensation are N,N'-dicyclohexylcarbodiimide, 1-ethyl-3-(3-dimethylaminopropyl)carbodiimide, etc. The other reaction conditions including reaction solvents, bases and reaction temperatures are similar to those set forth in Process 5.

Process 7

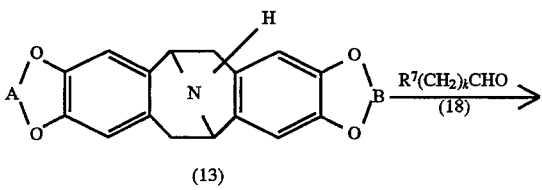

(13)

(19)

wherein A, B, $R^7$ and k are as defined above.

The compound represented by general formula (19) corresponding to the compound of general formula (1), wherein substituent $R^1$ is a group represented by formula —$CH_2$ $(CH_2)_kR^7$, can be prepared, e.g., by reacting the amine derivative shown by general formula (13) with an aldehyde shown by general formula (18), in an inert solvent in the presence of a reducing agent for reductive amination.

Examples of the solvent used for the above reaction include alcohol such as methanol or ethanol; hydrocarbons such as benzene, toluene or hexane; halogenated hydrocarbons such as dichloromethane, chloroform or dichloroethane; ethers such as tetrahydrofuran, dioxane or diethyl ether. Examples of the reducing agent used for the above reaction include hydride compounds such as lithium aluminum hydride, sodium cyanoborohydride, and sodium borohydride. These solvent and reducing agent may be used in an appropriate combination thereof.

In the reaction above, a proportion of the amino derivative to the aldehyde is not particularly limited. In general, the aldehyde may be used appropriately between the equimolar amount and more than the equimolar amount, based on the amino derivative. Preferably, the reactants are used in an almost equimolar amount. The reaction is carried out at a temperature ranging from ice cooling to about the boiling point of the solvent used.

Process 8

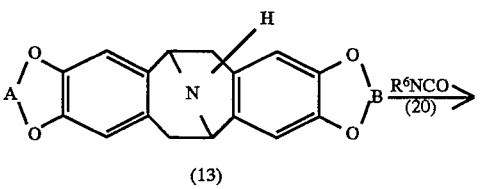

(13)

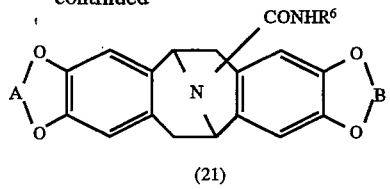

(21)

wherein A, B and $R^6$ have the same significance as defined above.

The compound represented by general formula (21) corresponding to the compound of general formula (1), wherein substituent $R^1$ is a group represented by formula $CONHR^6$, can be prepared, e.g., by reacting the amino derivative shown by general formula (13) with an isocyanate shown by general formula (20) in an inert solvent.

Examples of the solvent used are aprotic polar solvents such as N,N-dimethylformamide, dimethylsulfoxide, hexamethylphosphoramide or acetonitrile; hydrocarbons such as benzene, toluene or hexane; halogenated hydrocarbons such as dichloromethane, chloroform or dichloroethane; and ethers such as tetrahydrofuran, dioxane or diethyl ether.

In the reaction above, a proportion of the amino derivative of formula (13) to the isocyanate of formula (20) is not particularly limited. In general, the isocyanate of formula (20) is used appropriately chosen between the equimolar amount and more than the equimolar amount, based on the amino derivative. Preferably, the reactants are used in an almost equimolar amount. The reaction is carried out at a temperature ranging from ice cooling to about the boiling point of the solvent used.

The dicatechol compound shown by general formula (3) which is one of the starting compounds for producing the compounds of the present invention may be prepared, e.g., by the following process.

Process 9

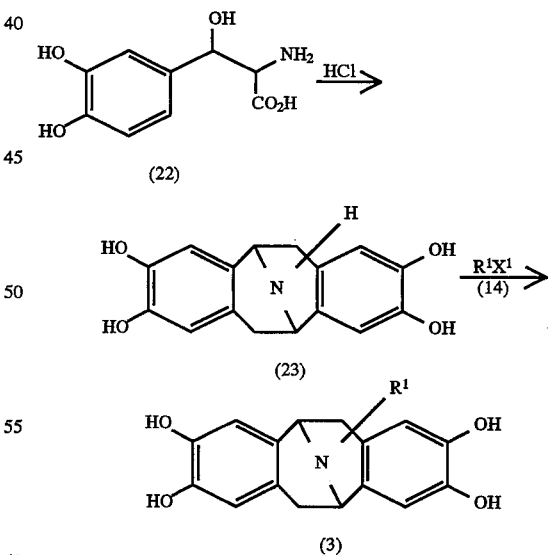

wherein $R^1$ and $X^1$ are as defined above.

The dicatechol compound of formula (3) may be prepared by heating 3,4-dihydroxyphenylserine shown by formula (22) with hydrochloric acid and then reacting the resulting amino compound of formula (23) with the halide of general formula (14), in a manner similar to Process 5.

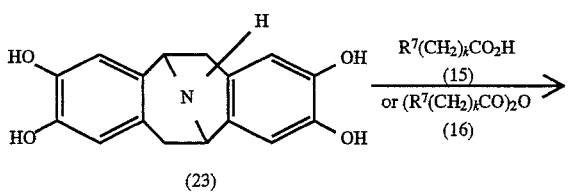

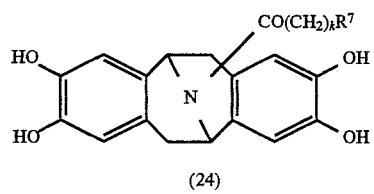

wherein R⁷ and k are as defined above.

The compound of general formula (24) corresponding to the compound of general formula (3), wherein substituent $R^1$ is a group represented by formula $-CO(CH_2)_kR^7$, may be prepared either by condensing the compound of formula (23) with the carboxylic acid shown by general formula (15) or by reacting the compound (23) with the acid anhydride shown by general formula (16), in a manner similar to Process 6.

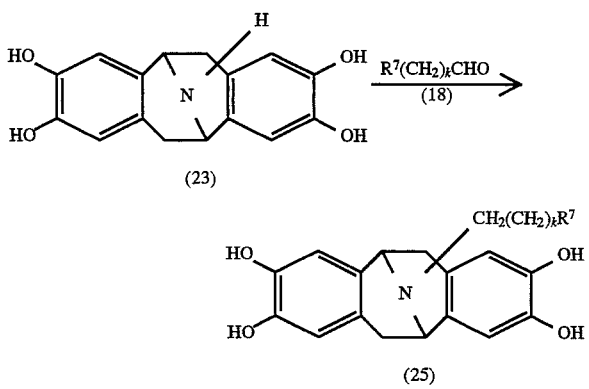

wherein R⁷ and k are as defined above.

The compound of general formula (25) corresponding to the compound of general formula (3), wherein substituent $R^1$ is a group represented by formula $-CH_2(CH_2)_kR^7$, may also be prepared by reductive amination of the aldehyde shown by general formula (18), in a manner similar to Process 7.

In the process described above, when $R^1$, A or B of the compound of general formula (1) possess one or more functional group(s) such as an amino group, an alkylamino group or a hydroxyl group, such group(s) can be protected by protective group(s) before the each step(s) in Process 1 to 9, and deprotected after the each step(s), if necessary or desired.

Such a protection-deprotection technique is described in, for example, T. W. Greene, "Protective Groups in Organic Synthesis" John Willey & Sons Inc., 1981.

The "protective group" includes following groups;

1) Protective group for an amino group or an alkylamino group
   an alkanoyl group such as an acetyl group
   an aroyl group such as a benzoyl group
   a tert-butoxycarbonyl group
   a benzyloxycarbonyl group
   a phthaloyl group (only for an amino group)
2) protective group for a hydroxyl group
   an alkanoyl group such as an acetyl group
   an aroyl group such as a benzoyl group
   a benzyl group
   a methoxymethyl group
   a trimethylsilyl group
   a tetrahydropyranyl group
   a tetrahydrofuranyl group Hereinafter the present invention will be described in more detail by referring to the following examples but is not deemed to be limited thereto.

EXAMPLE 1

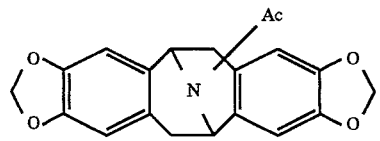

A mixture of 40 g of 13-acetyl-5, 6, 11, 12-tetrahydrodibenzo[a,e]cycloocten-5,11-imine-2, 3, 8, 9-tetrol, 119 g of cesium carbonate, 47.4 g of bromochloromethane and 600 ml of N,N-dimethylformamide was heated at 100° C. with stirring in a nitrogen atmosphere. Three hours after, insoluble salts were filtered off and the filtrate was concentrated in vacuo. The residue was partitioned between ethyl acetate and water, and the organic phase was dried over sodium sulfate. The solvent was distilled off in vacuo. The residue was purified by silica gel column chromatography (eluent, dichloromethane:ethyl acetate=9:1). The product was dissolved in a small quantity of methanol and water was added to the solution for trituration to give 28 g of 15-acetyl-5,6,12,13-tetrahydrocycloocta[1,2-f:5,6-f']bis[1,3]benzodioxol-5,12-imine. Melting point: 144°–145° C.

The starting 13-acetyl-5,6,11,12-tetrahydrodibenzo[a,e]cycloocten-5,11-imine-2,3,8,9-tetrol was prepared as follows.

A mixture of 600 g of 3-(3,4-dihydroxyphenyl)serine and 3.6 liters of 1N hydrochloric acid was heated at 90° C. with stirring in a nitrogen atmosphere. Five hours after, the reaction solution was cooled and then allowed to stand overnight. The formed crystals were filtered.

The crude product was warmed in a mixture of 600 ml of acetone and 2 liters of acetonitrile. Insoluble crystals were filtered to give 275 g of 5,6,11,12-tetrahydrodibenzo[a,e]cycloocten-5,11-imine-2,3,8,9-tetrol hydrochloride:

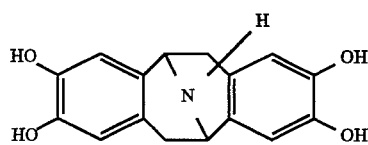

Melting point: 225°–229° C.

Then, 50 g of 5,6,11,12-tetrahydrodibenzo[a,e]cycloocten-5,11-imine-2,3,8,9-tetrol hydrochloride and 94.11 g of triethylamine were dissolved in 500 ml of N,N-dimethylformamide. Under cooling on an ice bath, 79.12 g of acetic anhydride was dropwise added to the solution over 30 minutes in a nitrogen atmosphere. The mixture was stirred at room temperature for further 5 hours. The salt formed was filtered off and the filtrate was concentrated in vacuo. The residue was crystallized from ethanol to give 73.15 g of 2,3,8,9-tetraacetoxy-13-acetyl-5,6,11,12-tetrahydrodibenzo[a,e]cycloocten-5,11-imine:

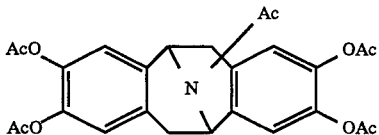

Melting point, 236°–237° C.

A mixture of 73 g of 2,3,8,9-tetraacetoxy-13-acetyl-5,6,11,12-tetrahydro-dibenzo[a,e]cycloocten-5,11-imine, 10 g of potassium carbonate and 1 liter of methanol was then heated at 40° C. with stirring in a nitrogen atmosphere. Thirty minutes after, the reaction mixture was rendered acidic with acetic acid followed by concentration in vacuo. The residue was dissolved in a small quantity of methanol and water was added to the solution for trituration. The product was filtered to give 48 g of 13-acetyl- 5,6,11,12-tetrahydrodibenzo[a,e]cycloocten-5,11-imine-2,3,8,9-tetrol:

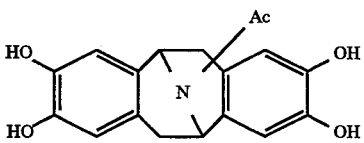

Melting point, 294°–296° C. (dec.).

EXAMPLE 2

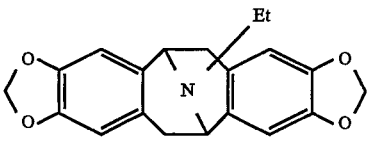

A mixture of 300 mg of 13-ethyl-5,6,11,12-tetrahydrodibenzo[a,e]cycloocten-5,11-imine-2,3,8,9-tetrol hydrochloride, 1.3 g of cesium fluoride, 333 mg of dibromomethane and 6 ml of N,N-dimethylformamide was heated at 110° C. with stirring in a nitrogen atmosphere. An hour and a half later, the reaction mixture was concentrated in vacuo. The residue was partitioned between diethyl ether and 1N sodium hydroxide and the organic phase was washed with water. After the organic phase was dried over sodium sulfate, the solvent was distilled off in vacuo. The residue was purified by preparative TLC (developing solvent, dichloromethane:methanol=50:1). The product was dissolved in ethanol and hydrogen chloride/diethyl ether solution (about 7%) was added to the solution. The formed salt was filtered to give 22 mg of 15-ethyl-5,6,12,13-tetrahydrocycloocta[1,2-f:5,6-f']bis[1,3]benzodioxol-5,12-imine hydrochloride. Melting point: 284°–288° C. (dec.).

The starting 13-ethyl-5,6,11,12-tetrahydrodibenzo[a,e]cycloocten-5,11-imine-2,3,8,9-tetrol hydrochloride was prepared as follows.

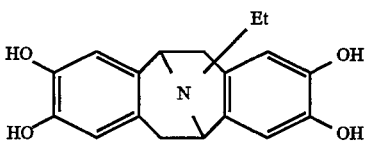

After 3 g of 5,6,11,12-tetrahydrodibenzo[a,e]-cycloocten-5,11-imine-2,3,8,9-tetrol hydrochloride was dissolved in 28 ml of methanol, 535 mg of acetaldehyde and 1.18 g of sodium cyanoborohydride were added to the solution. The mixture was stirred at room temperature overnight in a nitrogen atmosphere. Furthermore 206 mg of acetaldehyde and 294 mg of sodium cyanoborohydride were added to the reaction mixture. After the reaction was continued for 6 hours, conc. hydrochloric acid was added to the mixture to render the system acidic.

The solvent was distilled off in vacuo. The residue was crystallized from water to give 1.45 g of 13-ethyl-5,6,11,12-tetrahydrodibenzo[a,e]cycloocten-5,11-imine-2,3,8,9-tetrol hydrochloride. Melting point, 245°249° C. (dec.).

EXAMPLE 3

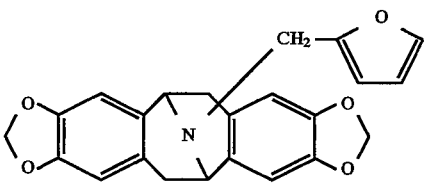

In a manner similar to Example 2, 20 mg of 15-furfuryl-5,6,12,13-tetrahydrocycloocta[1,2-f:5,6-f']bis[1,3]benzodioxol-5,12-imine hydrochloride was obtained from 200 mg of 13-furfuryl-5,6,11,12-tetrahydrodibenzo[a,e]cycloocten-5,11-imine-2,3,8,9-tetrol hydrochloride. Melting point, 225°–228° C. (dec.). The starting 13-furfuryl-5,6,11,12-tetrahydrodibenzo[a,e]cycloocten-5,11-imine-2,3,8,9-tetrol hydrochloride was prepared as follows.

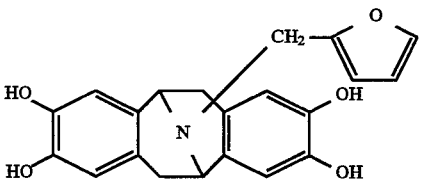

After 2.5 g of 5,6,11,12-tetrahydrodibenzo[a,e]cycloocten-5,11-imine-2,3,8,9-tetrol hydrochloride was dissolved in 23 ml of methanol, 1.12 g of furfural and 979 mg of sodium cyanoborohydride were added to the solution. The mixture was stirred at room temperature overnight in a nitrogen atmosphere. Furthermore 748 mg of furfural was added to the reaction mixture. After the reaction was continued for 8 hours, the reaction mixture was concentrated in vacuo. The residue was dissolved in water. While carefully adding sodium hydrogencarbonate to the solution, the system was rendered basic followed by extraction with ethyl acetate. After washing with water, the organic phase was dried over sodium sulfate and the solvent was distilled off in vacuo. The residue was dissolved in a small quantity of methanol and hydrogen chloride/diethyl ether solution (about 7%) was added to the solution to render the system acidic. The salt formed from diethyl ether was filtered and recrystallized from methanol/diethyl ether to give 323 mg of 13-furfuryl-5,6,11,12-tetrahydrodibenzo[a,e]cycloocten-5,11-imine-2,3,8,9-tetrol hydrochloride. Melting point, 235°–240° C. (dec.).

EXAMPLE 4

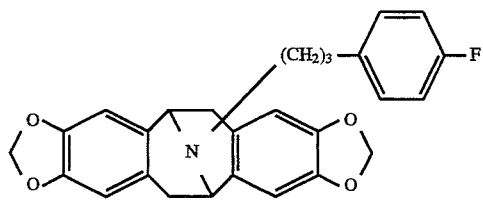

In a manner similar to Example 2, 34 mg of 15-[3-(4-fluorophenyl)propyl]-5,6,12,13-tetrahydrocycloocta[1,2-f:5,6-f']bis[1,3]benzodioxol-5,12-imine hydrochloride was obtained from 350 mg of 13-[3-(4-fluorophenyl)propyl]-5,6,11,12-tetrahydrodibenzo[a,e]cycloocten-5,11-imine-2,3,8,9-tetrol hydrochloride. Melting point, 155°–157° C.

The starting 13-[3-(4-fluorophenyl)propyl]-5,6,11,12-tetrahydrodibenzo[a,e]cyclooctene-5,11-imine-2,3,8,9-tetrol hydrochloride was prepared as follows.

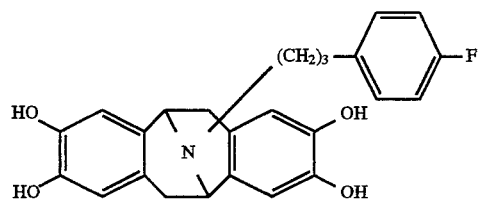

After 2.5 g of 5,6,11,12-tetrahydrodibenzo-[a,e]cycloocten-5,11-imine-2,3,8,9-tetrol hydrochloride was dissolved in 23 ml of methanol, 1.54 g of 3-(4-fluorophenyl)propanal and 979 mg of sodium cyanoborohydride were added to the solution. The mixture was stirred at room temperature overnight in a nitrogen atmosphere. Furthermore 711 mg of 3-(4-fluorophenyl)propanal was added to the reaction mixture. After the reaction was continued for 8 hours, the reaction mixture was concentrated in vacuo. The residue was dissolved in water. While carefully adding sodium hydrogen carbonate to the solution, the system was rendered basic followed by extraction with ethyl acetate. After washing with water, the organic phase was dried over sodium sulfate and the solvent was distilled off in vacuo. The residue was dissolved in a small quantity of methanol and hydrogen chloride/diethyl ether solution (about 7%) was added to the solution to render the system acidic. The salt formed from diethyl ether was filtered to give 1.73 g of 13-[3-(4-fluorophenyl)propyl]-5,6,11,12-tetrahydrodibenzo-[a,e]cycloocten-5,11-imine-2,3,8,9-tetrol hydrochloride. Melting point, 182°–188° C. (dec.).

EXAMPLE 5

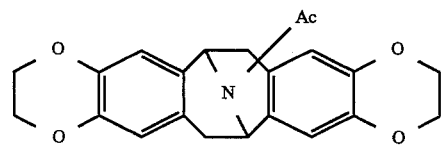

A mixture of 10 g of 13-acetyl-5,6,11,12-tetrahydrodibenzo[a,e]cycloocten-5,11-imine-2,3,8,9-tetrol, 42.8 g of potassium carbonate, 34.9 g of 1,2-dibromoethane and 186 ml of N,N-dimethylformamide was heated at 110° C. with stirring in a nitrogen atmosphere. Thirty hours after, insoluble salts were filtered off and the filtrate was concentrated in vacuo. The residue was partitioned between dichloromethane and water, and the organic phase was dried over sodium sulfate. The solvent was distilled off in vacuo. The residue was purified by silica gel column chromatography (eluent, dichloromethane:ethyl acetate=9:1). The product was dissolved in a small quantity of methanol and water was added to the solution for trituration to give 9.81 g of 17-acetyl-6,7,14,15-tetrahydrocycloocta[1,2-g:5,6-g']bis[1,4]benzodioxan-6,14-imine. Melting point: 170°–175° C.

EXAMPLE 6

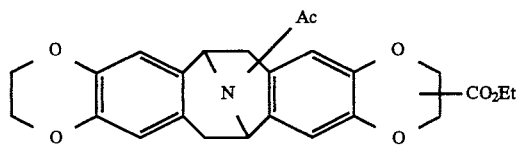

A mixture of 353 mg of 15-acetyl-6,7,12,13-tetrahydrobenzo[5,6]cycloocta[1,2-g]-1,4-benzodioxan-6,12-imine-9,10-diol, 415 mg of potassium carbonate, 299 mg of ethyl 2,3-dibromopropionate and 5 ml of N,N-dimethylformamide was heated at 100° C. with stirring in a nitrogen atmosphere. Three hours after, insoluble salts were filtered off and the filtrate was concentrated in vacuo. The residue was partitioned between dichloromethane and water and the organic phase was dried over sodium sulfate. The solvent was distilled off in vacuo. The residue was purified by silica gel column chromatography (eluent, chloroform:methanol=100:1). The product was dissolved in a small quantity of methanol and water was added to the solution for trituration to give 95 mg of a mixture of 17-acetyl-2-ethoxycarbonyl-6,7,14,15-tetrahydrocycloocta-[1,2-g:5,6-g']bis[1,4]-benzodioxan-6,14-imine and 17-acetyl-3-ethoxycarbonyl-6,7,14,15-tetrahydrocycloocta[1,2-g:5,6-g']bis[1,4]benzodioxan-6,14-imine. Melting point: 124°–128° C.

The starting 15-acetyl-6,7,12,13-tetrahydrobenzo[5,6]cycloocta[1,2-g]-1,4-benzodioxan-6,12-imine-9,10-diol was prepared as follows.

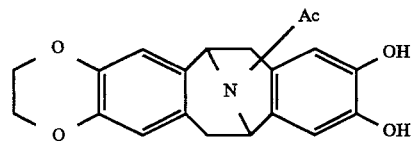

A mixture of 16 g of 13-acetyl-5,6,11,12-tetrahydrodibenzo[a,e]cycloocten-5,11-imine-2,3,8,9-tetrol, 7.45 g of potassium carbonate, 10.13 g of 1,2-dibromoethane and 240 ml of N,N-dimethylformamide was heated at 100° C. with stirring in a nitrogen atmosphere. Fifteen hours after, insoluble salts were filtered off and the filtrate was concentrated in vacuo. The residue was rendered acidic with 1N hydrochloric acid. The insoluble salts were filtered, dried and purified by silica gel column chromatography (eluent, dichloromethane:methanol=30:1). The product was recrystallized from methanol to give 3.91 g of 15-acetyl-6,7,12,13-tetrahydrobenzo-[5,6]cycloocta[1,2-g]-1,4-benzodioxan-6,12-imine-9,10-diol. Melting point: 192°–194° C.

EXAMPLE 7

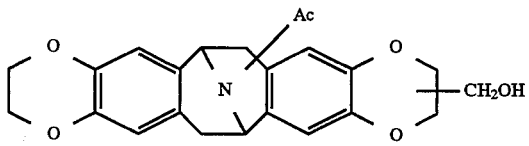

In a manner similar to Example 6, 303 mg of a mixture of 17-acetyl-6,7,14,15-tetrahydro-2-hydroxymethylcycloocta[1,2-g:5,6-g']bis[1,4]benzodioxan-6,14-imine and 17-acetyl-6,7,14,15-tetrahydro-3-hydroxymethylcycloocta[1,2-g: 5,6-g']bis[1,4]benzodioxan-6,14-imine was obtained from 600 mg of 15-acetyl-6,7,12,13-tetrahydrobenzo[5,6]cycloocta[1,2-g]-1,4-benzodioxan- 6,12-imine-9,10-diol and 165 mg of epichlorohydrin. Melting point, 172°–180° C.

EXAMPLE 8

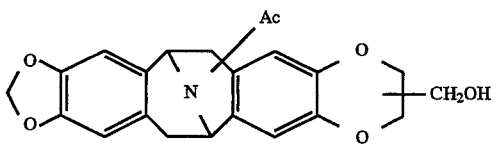

In a manner similar to Example 6, 2.63 g of a mixture of 16-acetyl-6,7,13,14-tetrahydro-2-hydroxymethyl[1,3]benzodioxolo[5,6-f]cycloocta[1,2-g]-1,4-benzodioxan-6,13-imine and 16-acetyl-6,7,13,14-tetrahydro-3-hydroxymethyl[1,3]benzodioxolo[5,6-f]cycloocta[1,2-g]-1,4-benzodioxan-6,13-imine was obtained from 4.5 g of 14-acetyl-5,6,11,12-tetrahydrobenzo[5,6]cycloocta[1,2-f]-1,3-benzodioxol-5,11-imine-8,9-diol and 1.29 g of epichlorohydrin. Melting point: 174°–182° C.

The starting 14-acetyl-5,6,11,12-tetrahydrobenzo[5,6]cycloocta[1,2-f]-1,3-benzodioxol-5,11-imine-8,9-diol was prepared as follows.

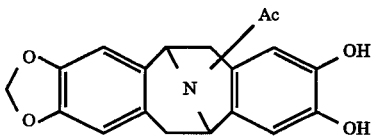

A mixture of 38 g of 13-acetyl-5,6,11,12-tetrahydrodibenzo[a,e]cycloocten-5,11-imine-2,3,8,9-tetrol, 39.4 g of cesium fluoride, 21.0 g of bromochloromethane and 540 ml of N,N-dimethylformamide was heated at 100° C. with stirring in a nitrogen atmosphere. Five hours and a half later, insoluble salts were filtered off and the filtrate was concentrated in vacuo. The residue was rendered acidic with 1N hydrochloric acid. The insoluble solids were filtered, dried and purified by silica gel column chromatography (eluent:dichloromethane:methanol=30:1).

The product was recrystallized from methanol to give 8.03 g of 14-acetyl-5,6,11,12-tetrahydrobenzo-[5,6]cycloocta[1,2-f]-1,3-benzodioxol-5,11-imine-8,9-diol. Melting point: 261°–265° C. (dec.).

EXAMPLE 9

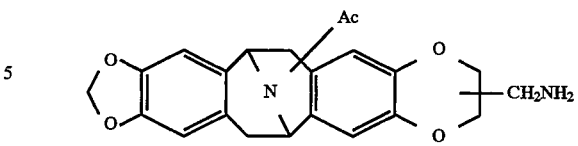

A mixture of 300 mg of an isomeric mixture of 16-acetyl-6,7,13,14-tetrahydro-2-(O-mesylmethyl)-[1,3]benzodioxolo[5,6-f]cycloocta[1,2-g]-1,4-benzodioxan-6,13-imine and 16-acetyl-6,7,13,14-tetrahydro-3-(O-mesylmethyl)-[1,3]benzodioxolo[5,8-f]cycloocta[1,2-g]-1,4-benzodioxan-6,13-imine, 3 ml of ammonium hydroxide (about 29% solution in water) and 3 ml of dioxane were heated at 80° C. in an autoclave. After heating for 6.5 hours, the reaction mixture was concentrated in vacuo and the residue was partitioned between dichloromethane and 2N hydrochloric acid. The aqueous phase was rendered basic with ammonia water. After extracting again with dichloromethane, the organic phase was dried over sodium sulfate. The solvent was distilled off in vacuo. The residue was crystallized from diethyl ether to give 158 mg of the isomeric mixture of 16-acetyl-2-aminomethyl-6,7,13,14-tetrahydro-[1,3]benzodioxolo[5,6-f]cycloocta[1,2-g]-1,4-benzodioxan-6,13-imine and 16-acetyl-3-aminomethyl-6,7,13,14-tetrahydro-[1,3]benzodioxolo[5,6-f]cycloocta[1,2-g]-1,4-benzodioxan-6,13-imine. Melting point: 180°–187° C.

This free amino compound was rendered acidic by adding a hydrogen chloride/diethyl ether solution (about 7%) to a solution of the amino compound in tetrahydrofuran. The resulting salt was thoroughly washed with diethyl ether to obtain the hydrochloride. Melting point: 235°–241° C.

The starting methanesulfonyl compound was prepared as follows.

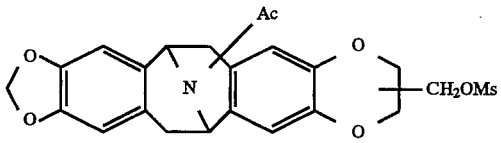

After 2 g of an isomeric mixture of 16-acetyl-6,7,13,14-tetrahydro-2-hydroxymethyl[1,3]benzodioxolo[5,6-f]cycloocta[1,2-g]-1,4-benzodioxan-6,13-imine and 16-acetyl-6,7,13,14-tetrahydro-3-hydroxymethyl[1,3]benzodioxolo[5,6-f]cycloocta[1,2-g]-1,4-benzodioxan-6,13-imine and 563 mg of triethylamine were dissolved in 30 ml of chloroform, 0.43 ml of methanesulfonyl chloride was dropwise added to the solution in a nitrogen atmosphere under cooling on an ice bath. Stirring was continued at the same temperature for 2 hours and then 256 mg of triethylamine and 0.2 ml of methanesulfonyl chloride were further added to the mixture. The resulting mixture was then allowed to stand overnight in a refrigerator. The reaction mixture was partitioned between chloroform and water, and the organic phase was dried over sodium sulfate. After the solvent was distilled off in vacuo, the residue was purified by silica gel column chromatography (eluent:dichloromethane:ethyl acetate=8:2). Thus, 2 g of the isomeric mixture of 16-acetyl-6,7,13,14-tetrahydro-2-(O-mesylmethyl)-[1,3]benzodioxolo-[5,6-f]cycloocta[1,2-g]-1,4-benzodioxan-6,13-imine and 16-acetyl-6,7,13,14-tetrahydro-3-(O-mesylmethyl)-[1,3]benzodioxolo[5,6-f]cycloocta[1,2-g]-1,4-benzodioxan-6,13-imine was obtained as a foamy substance.

EXAMPLES 10 to 12

The following compounds were obtained from methanesulfonyl compounds and amine derivatives in a manner similar to Example 9.

TABLE 1

| Example No. | R⁴ | R⁵ | Yield | M.P. |
|---|---|---|---|---|
| 10 hydrochloride | CH₃ | CH₃ | 95% | 198–205° C. |
| 11 hydrochloride | H | (CH₂)₂OH | 90% | 185–915° C. (dec.) |
| 12 hydrochloride | H | (CH₂)₂N(CH₃)₂ | 82% | 217–220° C. |

EXAMPLE 13

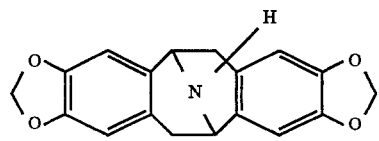

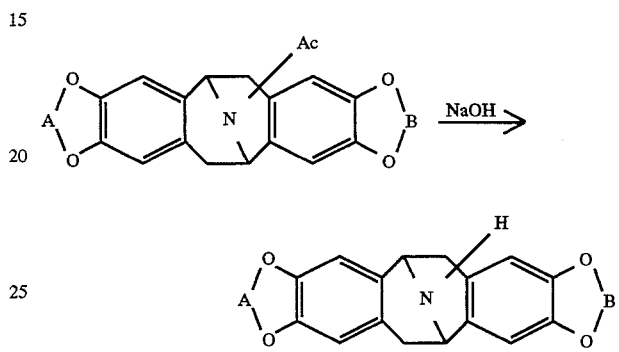

In a mixture of 250 ml of sodium hydroxide 12N solution in water and 250 ml of 2-methoxyethanol, 28 g of 15-acetyl-5,6,12,13-tetrahydrocycloocta[1,2-f:5,6-f']bis-[1,3]benzodioxol-5,12-imine was heated under reflux for 12 hours. Thereafter the reaction mixture was partitioned between dichloromethane and water. The organic layer was then washed with saturated sodium chloride aqueous solution. After drying over sodium sulfate, the organic phase was concentrated in vacuo. The residue was crystallized from methanol to give 14.2 g of 5,6,12,13-tetrahydrocycloocta-[1,2-f:5,6-f']bis[1,3]benzodioxol-5,12-imine. Melting point: 201°–202° C.

This free amino compound was converted into hydrochloride salt by adding a hydrogen chloride/diethyl ether solution (about 7%) to a solution of the amino compound in diethyl ether. The resulting salt was recrystallized from ethanol to obtain the hydrochloride. Melting point:>300° C.

EXAMPLES 14 to 16

The following compounds were prepared by hydrolysis in a manner similar to Example 13.

TABLE 2

| Example No. | A | B | Yield | M.P. |
|---|---|---|---|---|
| 14 Hydrochloride | -(CH₂)₂— | -(CH₂)₂— | 90% | 266–270° C. (dec.) |
| 15 Hydrochloride | -(CH₂)₂— | —CH₂CH(CH₂OH)— | 44% | 237–240° C. (dec.) |
| 16 Hydrochloride | -(CH₂)₂— | —CH₂CH(CH₂OH)— | 70% | 245–249° C. (dec.) |

EXAMPLE 17

After 309 mg of 5,6,12,13-tetrahydrocycloocta[1,2-f:5,6-f']bis[1,3]benzodioxol-5,12-imine and 21 mg of triethylamine were dissolved in 5 ml of chloroform, 0.1 ml of propionyl chloride was dropwise added to the solution in a nitrogen atmosphere under cooling on an ice bath. The mixture was stirred at the same temperature for 2 hours. The reaction mixture was then partitioned between chloroform and water, and the organic phase was dried over sodium sulfate. The solvent was distilled off in vacuo. The residue was purified by silica gel column chromatography (eluent, dichloromethane:ethyl acetate=25:1). The product was dissolved in a small quantity of methanol and water was added to the solution for trituration to give 330 mg of 5,6,12,13- tetrahydro-15-propionylcycloocta-[1,2-f:5,6-f']bis[1,3]benzodioxol-5,12-imine. Melting point: 202°–203° C.

EXAMPLES 18–39

The following compounds were prepared from the amino compounds and various halides in a manner similar to Example 17.

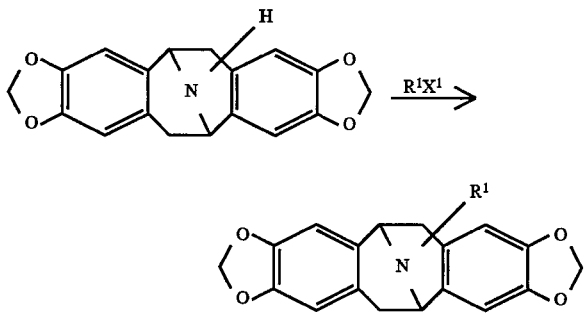

TABLE 3

| Compound No. | R¹ | X¹ | Yield (%) | Melting point |
|---|---|---|---|---|
| 18 | —CO(CH₂)₂CH₃ | Cl | 88 | 193–195° C. |
| 19 | —CO(CH₂)₄CH₃ | Cl | 74 | 175–176° C. |
| 20 | —COCH₂OCH₃ | Cl | 77 | 184–186° C. |
| 21 | —COCO₂CH₂CH₃ | Cl | 94 | 194–195° C. |
| 22 | —COCH₂CO₂CH₂CH₃ | Cl | 86 | 197–199° C. |
| 23 | —COPh | Cl | 98 | 271–273° C. |
| 24 | —CO₂CH₂CH₃ | Cl | 82 | 201–202° C. |
| 25 | —CO₂(CH₂)₄CH₃ | Cl | 83 | 180–181° C. |
| 26 | —CO₂Ph | Cl | 79 | 226–227° C. |
| 27 *2 | —CH₃ | I | 37 | 256–260° C. (dec.) |
| 28 *2 | —CH₂CH₃ | I | 88 | 284–288° C. (dec.) |
| 29 *2 | —(CH₂)₂CH₃ | I | 59 | 155–156° C. |
| 30 *2 | —(CH₂)₃CH₃ | Br | 50 | 270–275° C. (dec.) |
| 31 *2 | —CH₂CH(CH₃)₂ | Br | 78 | 266–267° C. |
| 32 *2 | —CH₂CH=CH₂ | Br | 88 | 207–210° C. (dec.) |
| 33 *2 | —(CH₂)₃CH=CH₂ | Br | 85 | 256–259° C. (dec.) |
| 34 *2 | *1 | Cl | 84 | 255–256° C. (dec.) |
| 35 *2 | —(CH₂)₂OH | Br | 99 | 269–272° C. (dec.) |
| 36 *2 | —(CH₂)₂CO₂CH₃ | Br | 55 | 231–232° C. (dec.) |
| 37 *2 | —CH₂CO₂CH₂CH₃ | Br | 68 | 142–145° C. |
| 38 *2 | —(CH₂)₂CO₂CH₂CH₃ | Br | 45 | 262–265° C. (dec.) |
| 39 *2 | —(CH₂)₂CN | Cl | 35 | 191–195° C. (dec.) |

*1: group shown below

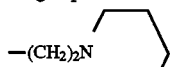

*2: hydrochloride

EXAMPLE 40

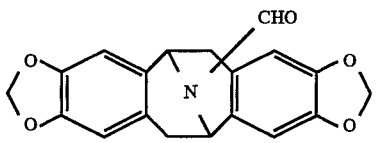

After 309 mg of 5,6,12,13-tetrahydrocycloocta-[1,2-f:5,6-f']bis[1,3]benzodioxol-5,12-imine, 55 mg of formic acid and 297 mg of 4-dimethylaminopyridine were dissolved in 20 ml of dimethylformamide, 466 mg of 1-ethyl-3-(3'-dimethylaminopropyl)carbodiimide hydrochloride was added to the solution in a nitrogen atmosphere under cooling on an ice bath. After reverting to room temperature, the mixture was stirred overnight. The reaction mixture was concentrated in vacuo. The residue was then partitioned between dichloromethane and 1N hydrochloric acid, followed by washing with water. The organic phase was dried over sodium sulfate. The solvent was distilled off in vacuo and the residue was purified by silica gel column chromatography (eluent, dichloromethane:ethyl acetate=19:1). The product was dissolved in a small quantity of methanol and water was added to the solution for trituration to give 285 mg of 15-formyl-5,6,12,13-tetrahydrocycloocta[1,2-f:5,6-f']bis[1,3]benzodioxol-5,12-imine- Melting point: 141°–146° C.

EXAMPLE 41

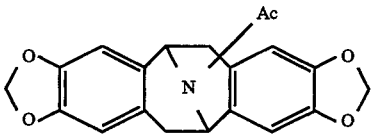

After 1.3 g of 5,6,12,13-tetrahydrocycloocta[1,2-f:5,6-f']bis[1,3S]benzodioxol-5,12-imine and 510 mg of triethylamine were dissolved in 21 ml of chloroform, 472 mg of acetic anhydride was dropwise added to the solution in a nitrogen atmosphere under cooling on an ice bath. At the same temperature, the mixture was stirred for 2 hours. The reaction mixture was then partitioned between chloroform and water and the organic phase was dried over sodium sulfate. The solvent was distilled off in vacuo and the residue was purified by silica gel column chromatography (eluent, dichloromethane:ethyl acetate=9:1). The product was dissolved in a small quantity of methanol and water was added to the solution for trituration to give 1.3 g of 15-acetyl-5,6,12,13-tetrahydrocycloocta[1,2-f:5,6-f']bis[1,3]benzodioxol-5,12-imine. Melting point: 144°–145° C.

EXAMPLE 42

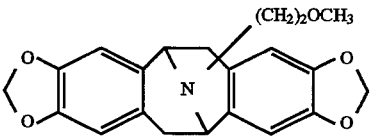

After 346 mg of 5,6,12,13-tetrahydrocycloocta-[1,2-f:5,6-f']bis[1,3]benzodioxol-5,12-imine hydrochloride and 192 mg of methoxyacetaldehyde (70% aqueous solution) were dissolved in methanol, 165 mg of sodium cyanoborohydride was added to the solution at room temperature. The mixture was stirred at the same temperature overnight. The reaction mixture was then concentrated in vacuo. The residue was partitioned between ethyl acetate and water and the organic phase was dried over sodium sulfate. The solvent was distilled off in vacuo. The residue was purified by silica gel column chromatography (eluent, dichloromethane:ethyl acetate=9:1). The product was recrystallized from methanol to give 330 mg of 5,6,12,13-tetrahydro-15-(2-methoxyethyl)cycloocta[1,2-f:5,6-f']bis[1,3]benzodioxol-5,12-imine. Melting point: 187°–188° C.

This free amino compound was rendered acidic by adding a hydrogen chloride/diethyl ether solution (about 7%) to a solution of the amino compound in dichloromethane. The resulting salt was thoroughly washed with diethyl ether to obtain the hydrochloride. Melting point: 240°–244° C. (dec.).

EXAMPLE 43

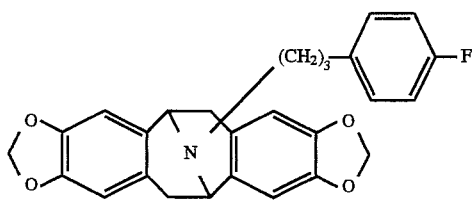

In a manner similar to Example 42, 356 mg of 15-[3-(4-fluorophenyl)propyl]-5,6,12,13-tetrahydrocycloocta[1,2-f:5,6-f']bis[1,3]benzodioxol-5,12-imine hydrochloride was obtained from 346 mg of 5,6,12,13-tetrahydrocycloocta[1,2-f:5,6-f']bis[1,3]benzodioxol-5,12-imine and 228 mg of 3-(4-fluorophenyl)propanal- Melting point: 147°–148° C.

EXAMPLE 44

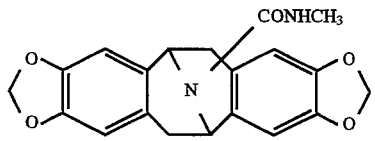

After 309 mg of 5,6,12,13-tetrahydrocycloocta[1,2-f:5,6-f']bis[1,3]benzodioxol-5,12-imine was dissolved in 5 ml of chloroform, 0.06 ml of methyl isocyanate was dropwise added to the solution in a nitrogen atmosphere under cooling on an ice bath. Two hours after, the precipitates formed were filtered and recrystallized from methanol to give 316 mg of 5,6,12,13-tetrahydro-15-(N-methylcarbamoyl)cycloocta[1,2-f:5,6-f']bis[1,3]benzodioxol-5,12-imine. Melting point: 254°–256° C.

EXAMPLE 45

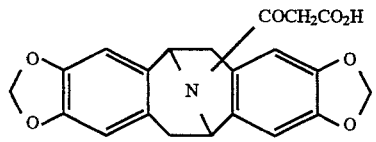

In a mixture 5 ml of sodium hydroxide 1N solution in water, 10 ml of water and 10 ml of tetrahydrofuran was stirred 1 g of 15-(ethoxycarbonylacetyl)-5,6,12,13-tetrahydrocycloocta[1,2-f:5,6-g']bis[1,3]benzodioxol-5,12-imine obtained in Example 22. An hour after, the reaction solution was partitioned between ethyl acetate and 4N hydrochloric acid. The extract was further washed with saturated sodium chloride aqueous solution. After the organic phase was dried over sodium sulfate, the solvent was distilled off in vacuo.

The residue was dissolved in a small quantity of methanol and water was added to the solution for trituration to give 820 mg of 15-(carboxyacetyl)-5,6,12,13-tetrahydrocycloocta[1,2-f:5,6-f']bis[1,3]benzodioxol-5,12-imine. Melting point: 154°–159° C.

EXAMPLE 46

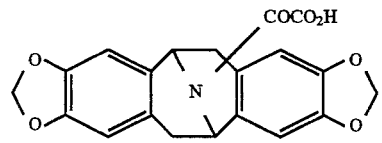

In a manner similar to Example 45, 295 mg of 5,6,12,13-tetrahydro-15-oxalocycloocta[1,2-f:5,6-f']bis[1,3]benzodioxol-5,12-imine was obtained from 320 mg of 15-ethoxalyl-5,6,12,13-tetrahydrocycloocta[1,2-f:5,6-f']bis[1,3]benzodioxol-5,12-imine obtained in Example 21. Melting point: 183°–187° C.

EXAMPLE 47

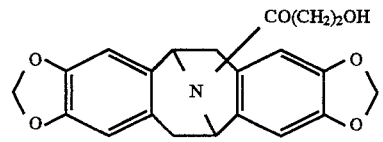

A solution of 4 g of 15-(ethoxycarbonylacetyl)-5,6,12,13-tetrahydrocycloocta[1,2-f:5,6-f']bis[1,3]benzodioxol-5,12-imine obtained in Example 22 in 50 ml of tetrahydrofuran was dropwise added over 30 minutes to a suspension of 206 mg of lithium borohydride in 50 ml of tetrahydrofuran, at room temperature in a nitrogen atmosphere. Stirring was then continued for further 5 hours. Then 1N hydrochloric acid was added to the reaction mixture to decompose an excess of lithium borohydride. The resulting mixture was concentrated in vacuo.

The residue was partitioned between dichloromethane and water and the organic phase was washed with saturated sodium chloride aqueous solution. After the organic phase was dried over sodium sulfate, the solvent was distilled off in vacuo. The residue was purified by silica gel column chromatography (eluent, dichloromethane:ethyl acetate= 9:1) to give as a foamy substance 1.32 g of 5,6,12,13-tetrahydro-15-(3-hydroxypropionyl)cycloocta[1,2-f:5,6-f']bis[1,3]benzodioxol-5,12-imine.

EXAMPLE 48

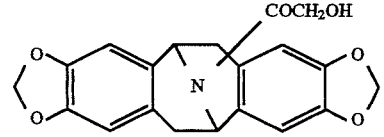

In a manner similar to Example 47, 194 mg of 15-glycoloyl-5,6,12,13-tetrahydrocycloocta[1,2-f:5,6-f']bis-[1,3]benzodioxol-5,12-imine was obtained from 409 mg of 15-ethoxalyl-5,6,12,13-tetrahydrocycloocta[1,2-f:5,6-f']bis[1,3]benzodioxol-5,12-imine obtained in Example 21. Melting point: 184°–187° C.

EXAMPLE 49

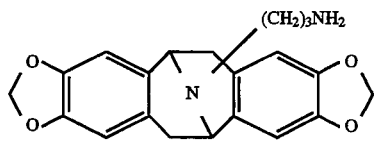

A solution of 300 mg of 15-(2-cyanoethyl)-5,6,12,13-tetrahydrocycloocta[1,2-f:5,6-f']bis[1,3]benzodioxol-5,12-imine in 5 ml of tetrahydrofuran was dropwise added to a suspension of 31 mg of lithium aluminum hydride in 1 ml of tetrahydrofuran over 20 minutes at room temperature in a nitrogen atmosphere. Stirring was then continued for further 5 hours. Then 1N sodium hydroxide was added to the reaction mixture to decompose an excess of lithium aluminum hydride. The mixture was filtered through celite. The filtrate was concentrated in vacuo. The residue was purified by silica gel column chromatography (eluent, methanol:ammonium hydroxide (29% aqueous solution)=50:1) to give as a foamy substance 50 mg of 15-(3-aminopropyl)-5,6,12,13-tetrahydrocycloocta[1,2-f:5,6-f']bis[1,S]benzodioxol-5,12-imine.

This free amino compound was rendered acidic by adding a hydrogen chloride/diethyl ether solution (about 7%) to a solution of the amino compound in tetrahydrofuran. The resulting salt was thoroughly washed with diethyl ether to obtain the hydrochloride. Melting point: 215°–220° C. (dec.).

EXAMPLE 50

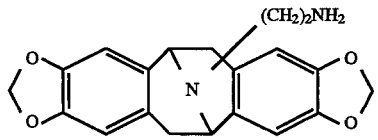

A mixture of 430 mg of 5,6,12,13-tetrahydro-15-(2-phthalimidoethyl)cycloocta[1,2-f:5,6-f']bis[1,3]benzodioxol-5,12-imine and 0.09 ml of hydrazine monohydrate was stirred in 6 ml of ethanol at room temperature. Eight hours after, the reaction mixture was concentrated in vacuo and the residue was partitioned between dichloromethane and saturated sodium bicarbonate aqueous solution. After the organic phase was extracted with 2N hydrochloric acid, the aqueous phase was rendered basic with sodium hydroxide 2N solution in water and extracted again with dichloromethane. After washing with water, the organic phase was dried over sodium sulfate. The solvent was distilled off in vacuo to give as a foamy substance 183 mg of 15-(2-aminoethyl)-5,6,12,13-tetrahydrocycloocta[1,2-f:5,6-f']bis[1,3]benzodioxol-5,12-imine.

This free amino compound was rendered acidic by adding a hydrogen chloride/diethyl ether solution (about 7%) to a solution of the amino compound in dichloromethane. The resulting salt was recrystallized from ethanol to obtain the hydrochloride. Melting point: 235°–240° C. (dec.).

The starting 5,6,12,13-tetrahydro-15-(2-phthalimidoethyl)cycloocta[1,2-f:5,6-f']bis[1,S]benzodioxol-5,12-imine:

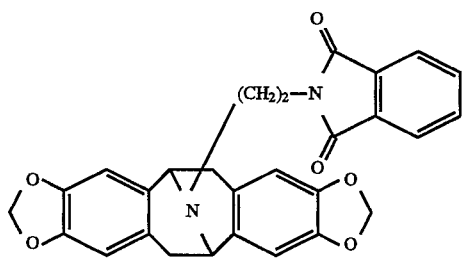

was obtained as a foamy substance from 450 mg of 5,6,12,13-tetrahydrocycloocta[1,2-f:5,6-f']bis[1,3]benzodioxol-5,12-imine and 424 mg of N-(2-bromoethyl)phthalimide in a manner similar to Example 17.

EXAMPLE 51

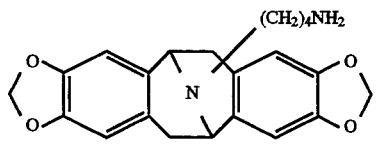

In a manner similar to Example 50, 210 mg of 15-(4-aminobutyl)-5,6,12,13-tetrahydrocycloocta[1,2-f:5,6-f']bis[1,3]benzodioxol-5,12-imine was obtained as a foamy substance from 400 mg of 5,6,12,13-tetrahydro-15-(4-phthalimidobutyl)cycloocta[1,2-f:5,6-f']bis[1,3]benzodioxol-5,12-imine.

This free amino compound was rendered acidic by adding a hydrogen chloride/diethyl ether solution (about 7%) to a solution of the amino compound in dichloromethane. The resulting salt was recrystallized from isopropyl alcohol-ethanol to obtain the hydrochloride. Melting point: 239°–243° C. (dec.).

The starting 5,6,12,13-tetrahydro-15-(4-phthalimidobutyl)cycloocta[1,2-f:5,6-f']bis[1,3]benzodioxol-5,12-imine:

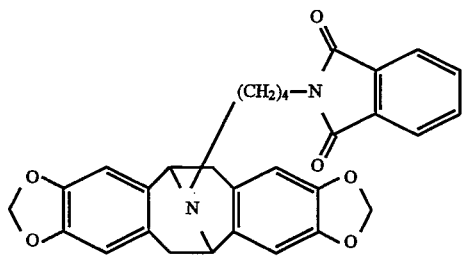

was obtained from 450 mg of 5,6,12,13-tetrahydrocycloocta[1,2-f:5,6-f']bis[1,3]benzodioxol-5,12-imine and N-(4-bromobutyl)phthalimide in a manner similar to Example 17, followed by recrystallization of the crude product from ethanol. The yield was 569 mg. Melting point: 151°–153° C.

EXAMPLE 52

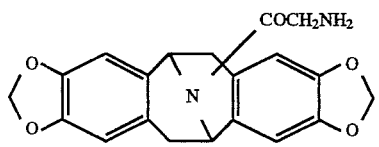

After 501 mg Of 15-(N-benzyloxycarbonylglycyl)-5,6, 12,13-tetrahydrocycloocta[1,2-f:5,6-f']bis[1,3]benzodioxol-5,12-imine was dissolved in a solvent mixture of 10 ml of methanol and 10 ml of tetrahydrofuran, 100 mg of 10% wet Pd/C was added to the solution. Hydrogenation was performed at room temperature under normal pressure. Four hours after, the reaction solution was filtered through celite and the solvent was distilled off in vacuo.

The residue was dissolved in a small quantity of methanol and water was added to the solution for trituration to give 341 mg of 15-glycyl-5,6,12,13-tetrahydrocycloocta[1,2-f:5, 6-f']bis[1,3]benzodioxol-5,12-imine. Melting point: 150°–153° C.

This free amino compound was rendered acidic by adding a hydrogen chloride/diethyl ether solution (about 7%) to a solution of the amino compound in dichloromethane. The resulting salt was thoroughly washed with diethyl ether to obtain the hydrochloride. Melting point: 243°–248° C. (dec.).

The starting 15-(N-benzyloxycarbonylglycyl)-5,6,12,13-tetrahydrocycloocta[1,2-f:5,6-f']bis[1,3]benzodioxol-5,12-imine:

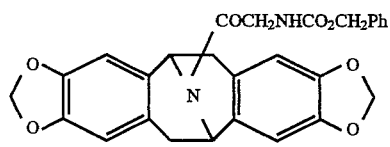

was obtained from 500 mg of 5,6,12,13-tetrahydrocycloocta[1,2-f:5,6-f']bis[1,3]benzodioxol-5,12-imine and 373 mg of benzyloxycarbonylglycine in a manner similar to Example 40. The yield was 664 mg. Melting point: 180°–181° C.

EXAMPLE 53

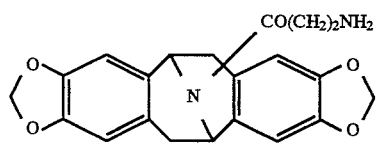

After 560 mg of 15-(3-N-t-butoxycarbonylaminopropionyl)-5,6,12,13-tetrahydrocycloocta[1,2-f:5,6-f']bis[1,3]benzodioxol-5,12-imine was dissolved in 5 ml of dichloromethane, 0.3 ml of trifluoroacetic acid was dropwise added to the solution in a nitrogen atmosphere under cooling on an ice bath.

Four hours after, the reaction mixture was partitioned between dichloromethane and 1N sodium hydroxide aqueous solution. The organic phase was washed with saturated sodium chloride aqueous solution. After the organic phase was dried over sodium sulfate, the solvent was distilled off in vacuo. The residue was crystallized from diethyl ether to give 412 mg of 15-(3-aminopropionyl)-5,6,12,13-tetrahydrocycloocta[1,2-f:5,6-f']bis[1,3]benzodioxol-5,12-imine. Melting point: 147°–154° C.

This free amino compound was rendered acidic by adding a hydrogen chloride/diethyl ether solution (about 7%) to a solution of the amino compound in tetrahydrofuran. The resulting salt was thoroughly washed with diethyl ether to obtain the hydrochloride. Melting point: 222°–225° C.

The starting 15-(3-N-t-butoxycarbonyl-aminopropionyl)-5,6,12,13-tetrahydrocycloocta[1,2-f:5,6-f']bis[1,3]benzodioxol-5,12-imine:

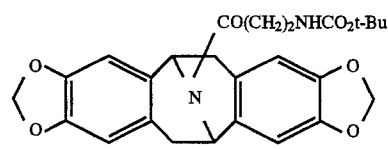

was obtained as a foamy substance from 620 mg of 5,6,12,13-tetrahydrocycloocta[1,2-f:5,6-f']bis[1,3]benzodioxol-5,12-imine and 454 mg of N-t-butoxycarbonyl-β-alanine in a manner similar to Example 40. The yield was 670 mg.

EXAMPLE 54

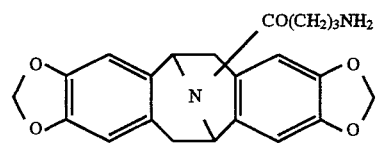

In a manner similar to Example 53, 431 mg of 15-(4-aminobutyryl)-5,6,12,13-tetrahydrocycloocta[1,2-f:5,6-f']bis[1,3]benzodioxol-5,12-imine was obtained from 560 mg of 15-(4-N-t-butoxycarbonyl-aminobutyryl)-5,6,12,13-tetrahydrocycloocta[1,2-f:5,6-f']bis[1,3]benzodioxol-5,12-imine. Melting point: 148°–152° C.

This free amino compound was rendered acidic by adding a hydrogen chloride/diethyl ether solution (about 7%) to a solution of the amino compound in tetrahydrofuran. The resulting salt was thoroughly washed with diethyl ether to obtain the hydrochloride. Melting point: 202°–205° C.

The starting 15-(4-N-t-butoxycarbonylaminobutyl)-5,6, 12,13-tetrahydrocycloocta[1,2-f:5,6-f']bis[1,3]benzodioxol-5,12-imine:

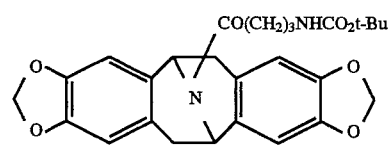

was obtained as a foamy substance from 620 mg of 5,6,12, 13-tetrahydrocycloocta[1,2-f:5,6-f']bis[1,3]benzodioxol-5, 12-imine and 488 mg of N-t-butoxycarbonyl-4-aminobutyric acid in a manner similar to Example 40. The yield was 620 mg.

EXAMPLE 55

Inhibitory effect on TNF production or secretion in mouse peritoneal macrophages (In case drug concentration is 30 μM)

BALB/c mice (5 weeks old, female. Charles River Japan) were intraperitoneally injected with 1 ml of 3% thioglycollate broth. After 4 days, the mice were sacrificed. Peritoneal exudated cells (PECs) were collected from the peritoneal cavity by washing with minimum essential medium (hereinafter abbreviated as MEM, manufactured by Handai Biseibutubyo Kenkyukai, Osaka, Japan) containing 5 U/ml heparin and 1% fetal bovine serum (FBS, manufactured by GIBCO Laboratories Inc.). PECs were washed three times with MEM, suspended with MEM containing 10% FBS. After the viable cells were counted by exclusion of trypan blue dye, the suspension was adjusted at the final concentration of $2 \times 10^6$ cells/ml with MEM containing 10% FBS and seeded into a 96-well microplate (Costar, Cambridge, Mass., USA) at $2 \times 10^5$ cells/100 µl/well. The PECs were incubated for an hour at 37° C. in a humidified 5% $CO_2$ incubator, and were washed twice with MEM warmed at 37° C. to remove non-adherent cells. Residual adherent cells were used as peritoneal macrophages. After the washing above, 50 µl each/well of MEM containing 10% FBS was added to each well and provided for use in the following experiment.

The powdery compound of the present invention was dissolved in dimethylsulfoxide in a concentration of 30 mM. The solution was then diluted with MEM containing 10% FBS in the final concentration of 30 µM. In the peritoneal macrophages obtained above, 50 µl each of the dilution was added to each well to make the total volume 100 µl. Thereafter 100 µl each of lipopolysaccharide (hereinafter abbreviated as LPS, E. coli 0111B4, manufactured by DIFCO, USA) was added to each well in the final concentration of 10 µg/ml. After the cells were incubated at 37° C. for 18 hours in a humidified 5% $CO_2$ incubator, 25 µl of the supernatant in each well was collected.

The TNF activity in the supernatant collected was determined by bioassay using TNF-sensitive mouse fibroblast cell line L929 cells. That is, 100 µl each of MEM containing 10% FBS was added to each well of a 96-well microplate; using the resulting mixture, 25 µl of the collected supernatant was diluted to 5-fold dilution to final concentrations (concentrations after the following addition of L929 cell suspension) of 10%, 2%, 0.4% and 0.08%.

L929 cells were then suspended ($4 \times 10^5$ cells/ml) in MEM containing 10% FBS and 1 µg/ml actinomycin D (Sigma Co.) and 100 µl each of the suspension was added to each well of the above microplate at $4 \times 10^4$ cells/well and cultured at 37° C. in a humidified 50% $CO_2$. The viable cells were counted by partial modification of the MTT method reported in Monosann et al., T., J. Immunol. Method, 65, 55–63, 1983. The modified MTT method comprises the following steps. One mg/ml of 3-(4,5-dimethylthiazol-2-yl)-2,5-diphenyltetrazolium bromide (hereinafter abbreviated as MTT, manufactured by Sigma Co.) was dissolved in MEM, and 50 µl each of the solution was added to each well of the microplate above. After incubating the microplate for further 6 hours, the supernatant was discarded and 100 µl of 0.004N HCl-isopropyl alcohol and then 10 µl of 0.01% sodium laurylsulfate aqueous solution was added to each well. After shaking the 96-well microplate for a few minutes, the absorbance in each well was measured with a microplate reader (Corona Co.) at an absorption wavelength of 550 nm. The absorbance correlated to the count of the viable L929 cells and represented the TNF activity in the supernatant. The TNF activity was determined in terms of unit (U)/ml from the calibration curve of absorbance for the TNF activity obtained using mouse recombinant TNF α (TNF-M, manufactured by Genzyme Co.) as a standard. The activity of inhibiting TNF production of each compound, was determined by the following equation.

Inhibition of TNF production or secretion (%)=(1−TNF activity in the supernatant of the treated cells/TNF activity in the supernatant of the non-treated cells)×100

The results are shown in Tables 4 through 6.

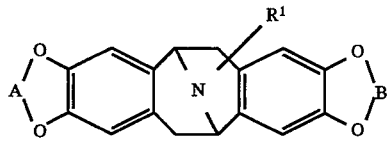

TABLE 4

| | | Inhibition of TNF Production or Secretion | | |
|---|---|---|---|---|
| Example No. | $R^1$ | A | B | Inhibition (%) |
| 1 | —COCH₃ | —CH₂— | —CH₂— | 95 |
| 2 Hydrochloride | —CH₂CH₃ | —CH₂— | —CH₂— | 72 |
| 3 Hydrochloride | CH₂-[furan] | —CH₂— | —CH₂— | −99 |
| 4 Hydrochloride | —(CH₂)₃-[phenyl]-F | —CH₂— | —CH₂— | 18 |
| 5 | —COCH₃ | —(CH₂)₂— | —(CH₂)₂— | 64 |
| 6 | —COCH₃ | —(CH₂)₂— | —CH₂CH(CO₂CH₂CH₃)— | 89 |
| 7 | —COCH₃ | —(CH₂)₂— | —CH₂CH(CH₂OH)— | 65 |
| 8 | —COCH₃ | —CH₂— | —CH₂CH(CH₂OH)— | 86 |
| 9 Hydrochloride | —COCH₃ | —CH₂— | —CH₂CH(CH₂NH₂)— | 69 |
| 10 | —COCH₃ | —CH₂— | —CH₂CH(CH₂N(CH₃)₂)— | 69 |

TABLE 4-continued

Inhibition of TNF Production or Secretion

| Example No. | R¹ | A | B | Inhibition (%) |
|---|---|---|---|---|
| 11 Hydrochloride | —COCH₃ | —CH₂— | —CH₂CH(CH₂NH(CH₂)₂OH)— | 61 |
| 12 Hydrochloride | —COCH₃ | —CH₂— | —CH₂CH(CH₂NH(CH₂)₂N(CH₃)₂)— | 57 |
| 13 Hydrochloride | —H | —CH₂— | —CH₂— | 78 |
| 14 Hydrochloride | —H | —(CH₂)₂— | —(CH₂)₂— | 63 |
| 15 Hydrochloride | —H | —CH₂— | —CH₂CH(CH₂OH)— | 55 |
| 16 Hydrochloride | —H | —(CH₂)₂— | —CH₂CH(CH₂OH)— | 18 |

TABLE 5

Inhibition of TNF Production or Secretion

| Example No. | R¹ | A | B | Inhibition (%) |
|---|---|---|---|---|
| 17 | —COCH₂CH₃ | —CH₂— | —CH₂— | 94 |
| 18 | —CO(CH₂)₂CH₃ | —CH₂— | —CH₂— | 86 |
| 19 | —CO(CH₂)₄CH₃ | —CH₂— | —CH₂— | 16 |
| 20 | —COCH₂OCH₃ | —CH₂— | —CH₂— | 92 |
| 21 | —COCO₂CH₂CH₃ | —CH₂— | —CH₂— | 69 |
| 22 | —COCH₂CO₂CH₂CH₃ | —CH₂— | —CH₂— | 77 |
| 23 | —COPh | —CH₂— | —CH₂— | 39 |
| 24 | —CO₂CH₂CH₃ | —CH₂— | —CH₂— | 68 |
| 25 | —CO₂(CH₂)₄CH₃ | —CH₂— | —CH₂— | 46 |
| 26 | —CO₂Ph | —CH₂— | —CH₂— | 27 |
| 27 | —CH₃ | —CH₂— | —CH₂— | 86 |
| 29 Hydrochloride | —(CH₂)₂CH₃ | —CH₂— | —CH₂— | 31 |
| 30 Hydrochloride | —(CH₂)₃CH₃ | —CH₂— | —CH₂— | −37 |
| 31 Hydrochloride | —CH₂CH(CH₃)₂ | —CH₂— | —CH₂— | 36 |
| 32 Hydrochloride | —CH₂CH=CH₂ | —CH₂— | —CH₂— | 12 |
| 33 Hydrochloride | —(CH₂)₃CH=CH₂ | —CH₂— | —CH₂— | −5 |
| 34 Hydrochloride |  | —CH₂— | —CH₂— | 56 |
| 35 Hydrochloride | —(CH₂)₂OH | —CH₂— | —CH₂— | 65 |
| 36 Hydrochloride | —(CH₂)₂CO₂CH₃ | —CH₂— | —CH₂— | −24 |
| 37 Hydrochloride | —CH₂CO₂CH₂CH₃ | —CH₂— | —CH₂— | 19 |

TABLE 6

Inhibition of TNF Production or Secretion

| Example No. | R¹ | A | B | Inhibition (%) |
|---|---|---|---|---|
| 38 Hydrochloride | -(CH₂)₂CO₂CH₂CH₃ | —CH₂— | —CH₂— | 6 |
| 39 Hydrochloride | -(CH₂)₂CN | —CH₂— | —CH₂— | −48 |
| 40 chloride | CHO | —CH₂— | —CH₂— | 84 |
| 42 | -(CH₂)₂OCH₃ | —CH₂— | —CH₂— | 11 |
| 44 | —CONHCH₃ | —CH₂— | —CH₂— | 90 |
| 45 | —COCH₂CO₂H | —CH₂— | —CH₂— | 15 | where R¹ is —(CH₂)₂—N attached to a piperidine ring (Example 34).

TABLE 6-continued

Inhibition of TNF Production or Secretion

| Example No. | R$^1$ | A | B | Inhibition (%) |
|---|---|---|---|---|
| 46 | —COCO$_2$H | —CH$_2$— | —CH$_2$— | 6 |
| 47 | —CO(CH$_2$)$_2$OH | —CH$_2$— | —CH$_2$— | 83 |
| 48 | —COCH$_2$OH | —CH$_2$— | —CH$_2$— | 85 |
| 49 Hydrochloride | -(CH$_2$)$_3$NH$_2$ | —CH$_2$— | —CH$_2$— | −4 |
| 50 Hydrochloride | -(CH$_2$)$_2$NH$_2$ | —CH$_2$— | —CH$_2$— | 64 |
| 51 Hydrochloride | -(CH$_2$)$_4$NH$_2$ | —CH$_2$— | —CH$_2$— | −44 |
| 52 Hydrochloride | —COCH$_2$NH$_2$ | —CH$_2$— | —CH$_2$— | 20 |
| 53 Hydrochloride | —CO(CH$_2$)$_2$NH$_2$ | —CH$_2$— | —CH$_2$— | −1 |
| 54 Hydrochloride | —CO(CH$_2$)$_3$NH$_2$ | —CH$_2$— | —CH$_2$— | 35 |

EXAMPLE 56

Inhibitory effect on TNF production in mouse peritoneal macrophages (In case drug concentrations is 50 µM and 100 µM)

The inhibitory effect of the inhibitors of the present invention against TNF production or secretion was examined at the final concentration of 50 µM or 100 µM in a manner similar to Example 55.

The results are shown in Table 7.

TABLE 7

| | Inhibition of TNF Production or secretion at 50 µM or 100 µM | |
|---|---|---|
| Example No. | Concentration of compound (µM) | Inhibition (%) |
| 19 | 100 | 51 |
| 29 Hydrochloride | 100 | 81 |
| 30 Hydrochloride | 50 | 41 |
| 30 Hydrochloride | 100 | 78 |
| 49 Hydrochloride | 50 | 21 |

The results of Table 7 reveal that by increasing the concentration of the compound, the inhibition can be enhanced even with the compounds having a small or negative value of the TNF inhibitory activity in Example 55.

EXAMPLE 57

Protective effect on endotoxin-induced death in galactosamine-treated mice

It is known that administration of LPS to mice induces a typical shock to cause sudden death of the animals. This model is thus considered to be an endotoxin-induced shock model.

It is also suggested that TNF would act as a major mediator for development of the disease in this model because a temporarily increased level of TNF in mouse blood is observed immediately after the administration of LPS, and death due to the shock is prevented by the administration of anti-TNF antibody [J. Immunol., 148, 1890–1897 (1992), Lymphokine and Cytokine Res., 10 (2), 127–131 (1991), and Science, 229 867–871 (1985)].

On the other hand, it is reported that the administration of galactosamine results in markedly increased sensitivity to LPS-induced shock so that galactosamine is often administered in combination with LPS in the endotoxin-induced shock model [Proc. Natl. Acad. Sci. USA, 76 (11), 5939–5943 (1979), Infect. Immun., 59 (6), 2110–2115 (1991), and J. Infect. Dis., 165, 501–505 (1992)].

In order to demonstrate the usefulness of the TNF inhibitors of the present invention in the endotoxin-induced shock, the following test was performed using the evaluation system described above.

Method

D-Galactosamine hydrochloride (hereinbelow abbreviated as D-galN, manufactured by Nakarai Tesque) and LPS were dissolved in water at final concentrations of 75 mg/ml and 0.2 µg/ml, respectively. Furthermore, the compound of the present invention was dissolved in a 5% dimethylsulfoxide-10% Nikkol (Nippon Surfactant Kogyo, Japan) solution at the final concentration of 5 mg/ml.

BALB/c mice (female, 5 weeks old) obtained from Charles River Japan, Inc. were injected i.v. with the aqueous solution containing D-galN and LPS described above in a dose of 200 µl/20 g body weight. The mice were divided groups of 10 mice. Immediately after the i.v. injection, the animals received i.p. injection with the compound of the present invention dissolved in the 5% dimethylsulfoxide-10% Nikkol solution in the concentration above in a dose of 200 µl/20 g body weight. Control animals received the same volume of the 5% dimethylsulfoxide-10% Nikkol aqueous solution alone.

The activity of the compound for protection of endotoxin-induced death in the galactosamine-treated mice is expressed in terms of the survival rate observed for the following last 7 days. The surviva rate expressed as the live/total ratio were statistically analyzed by X$^2$ method between the treated group and the control group.

Table 7 shows the activity of the respective compounds in the respective doses for protection of endotoxin-induced death in the galactosamine-treated mice.

TABLE 7

Protective effect on endotoxin-induced death in galactosamine-treated mice

| Compound No. (Example No.) | Dose (mg/kg) | Survival rate (%) |
|---|---|---|
| 1 | 0 | 30 |
| | 50 | 90* |
| 2 Hydrochloride | 0 | 0 |
| | 50 | 90* |
| 5 | 0 | 20 |
| | 50 | 30 |
| 13 Hydrochloride | 0 | 10 |
| | 50 | 95* |
| 14 Hydrochloride | 0 | 20 |
| | 50 | 30 |
| 17 | 0 | 20 |
| | 50 | 50 |
| 20 | 0 | 0 |
| | 50 | 0 |
| 21 | 0 | 20 |
| | 50 | 40 |

TABLE 7-continued

Protective effect on endotoxin-induced death in galactosamine-treated mice

| Compound No. (Example No.) | Dose (mg/kg) | Survival rate (%) |
| --- | --- | --- |
| 24 | 0 | 20 |
|  | 50 | 60 |
| 25 | 0 | 20 |
|  | 50 | 30 |
| 34 | 0 | 0 |
| Hydrochloride | 50 | 70* |
| 35 | 0 | 0 |
| Hydrochloride | 50 | 90* |
| 40 | 0 | 20 |
|  | 50 | 60 |
| 50 | 0 | 20 |
| Hydrochloride | 50 | 100* |

*P<0.01

Preparation Example 1

Tablet is prepared, e.g., by the following procedure.

|  |  | mg/tablet |
| --- | --- | --- |
| 1 | Compound of Example 50, hydrochloride | 10 |
| 2 | Lactose | 72.5 |
| 3 | Corn starch | 30 |
| 4 | Carboxymethyl cellulose Calcium | 5 |
| 5 | Hydroxypropyl cellulose (HPC-L) | 2 |
| 6 | Magnesium stearate | 0.5 |
|  | Total | 120 mg |

The components 1–4 are mixed, agglomerated with aqueous solution of component 5, and then mixed with component 6. The resulting mixture is compacted into a tablet of 120 mg.

Preparation Example 2

Injection is prepared, e.g., by the following procedure.
Compound of Example 50, hydrochloride 10 mg/vial
Saline 10 ml/vial A solution of the above components is sterilized by filteration, filled in a vial previously washed and sterilized. The vial is plugged with a rubber stopper washed and sterilized, and then sealed with a flip-off-cap to prepare an injection.

What is claimed is:

1. A method for inhibiting the production or secretion of tumor necrosis factor in a patient in need of such inhibition, which comprises administering to the patient a pharmaceutically effective amount of a compound represented by formula (1):

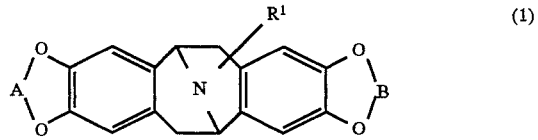

wherein $R^1$ represents a hydrogen atom, a straight or branched alkyl group having 1 to 6 carbon atoms, a straight or branched alkenyl group having 2 to 6 carbon atoms, a straight or branched alkanoyl group having 1 to 6 carbon atoms, an aroyl group having not more than 11 carbon atoms, or a group shown by formula:

$-X^1-(CH_2)_kR^7$ wherein $R^7$ represents a halogen atom, a hydroxyl group, a straight or branched alkoxy group having 1 to 6 carbon atoms, a straight or branched alkylthio group having 1 to 6 carbon atoms, a carboxyl group, a straight or branched alkoxycarbonyl group having 2 to 6 carbon atoms, an aryloxycarbonyl group having 7 to 13 carbon atoms, a cyano group, an amino group, an alkylamino group having 1 to 4 carbon atoms, a dialkylamino group having 2 to 8 carbon atoms, a cycloalkyl group having 3 to 7 carbon atoms, or an aromatic hydrocarbon group having not more than 10 carbon atoms; $X^1$ represents a carbonyl group or a methylene group; k represents 0 or an integer of 1 to 5, provided that when $X^1$ is a carbonyl group and $R^7$ is a hydroxyl group, or when $X^1$ is a methylene group and $R^7$ is a hydroxyl group, an amino group, an alkylamino group or a dialkylamino group, k represents an integer of 1 to 5; and each of A and B independently represents a methylene group or a group shown by:

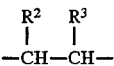

wherein each of $R^2$ and $R^3$ independently represents a hydrogen atom, alkoxycarbonyl group, an unsubstituted alkyl group, or an alkyl group having 1 to 3 carbon atoms substituted with a hydroxy group, an amino group, an alkylamino group having 1 to 4 carbon atoms, or a dialkylamino group having 2 to 8 carbon atoms; or a pharmaceutically acceptable salt thereof.

2. A method according to claim 1, wherein $R^1$ is a hydrogen atom, a straight or branched alkyl group having 1 to 6 carbon atoms, a straight or branched alkanoyl group having 1 to 6 carbon atoms, an aroyl group having not more than 11 carbon atoms, or a group shown by formula $-X^1-(CH_2)_kR^7$, wherein $R^7$, $X^1$ and k are as defined in claim 1.

3. A method according to claim 2, wherein k is 0, 1 or 2.

4. A method according to claim 3, wherein $R^1$ is a hydrogen atom, a straight or branched alkyl group having 1 to 6 carbon atoms, a straight or branched alkanoyl group having 1 to 6 carbon atoms, an aroyl group having not more than 11 carbon atoms, or a group shown by formula $-X^1-(CH_2)_kR^7$;

wherein $R^7$ is a halogen atom, a hydroxyl group, a straight or branched alkoxy group having 1 to 6 carbon atoms, a straight or branched alkylthio group having 1 to 6 carbon atoms, a carboxyl group, a straight or branched alkoxycarbonyl group having 2 to 6 carbon atoms, an aryloxycarbonyl group having 7 to 13 carbon atoms, a cyano group, an alkylamino group having 1 to 4 carbon atoms, a dialkylamino group having 2 to 8 carbon atoms, a cycloalkyl group having 3 to 7 carbon atoms, or an aromatic hydrocarbon group having not more than 10 carbon atoms; and $X^1$ is a carbonyl group.

5. A method according to claim 3, wherein $R^1$ is a hydrogen atom, a straight or branched alkyl group having 1 to 6 carbon atoms, a straight or branched alkanoyl group having 1 to 6 carbon atoms, an aroyl group having not more than 11 carbon atoms, or a group shown by formula $-X^1-(CH_2)_kR^7$;

wherein $R^7$ is a halogen atom, a hydroxyl group, a straight or branched alkoxy group having 1 to 6 carbon atoms, a straight or branched alkylthio group having 1 to 6 carbon atoms, a carboxyl group, an aryloxycarbonyl group having 7 to 13 carbon atoms, an amino group, an alkylamino group having 1 to 4 carbon atoms, a dialkylamino group having 2 to 8 carbon atoms, or a cycloalkyl group having 3 to 7 carbon atoms; and $X^1$ is a methylene group.

6. A method according to claim 4, wherein A and B each represents a methylene group.

7. A method according to claim 5, wherein A and B each represents a methylene group.

8. The method according to any one of claims 1, 2, 3, 4, 5, 6 and 7, wherein said patient is afflicted with cachexia, septic shock, multiple organ failure, Rheumatoid Arthritis, inflammatory bowel disease, multiple sclerosis, Osteoarthritis, graft versus host disease (GvHD), malaria, or meningitis, each of which disease is caused by the excessive production or secretion of tumor necrosis factor.

9. The method according to claim 8, wherein said patient is afflicted with Rheumatoid arthritis.

10. A compound represented by general formula (1):

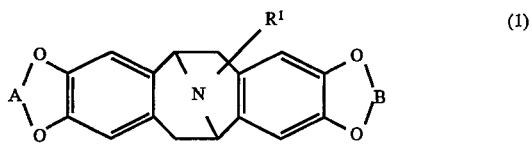
(1)

wherein $R^1$ represents a hydrogen atom, a straight or branched alkyl group having 1 to 6 carbon atoms, a straight or branched alkenyl group having 2 to 6 carbon atoms, a straight or branched alkanoyl group having 1 to 6 carbon atoms, an aroyl group having not more than 11 carbon atoms, or a group shown by formula:

—$X^1$—$(CH_2)_k R^7$ wherein $R^7$ represents a halogen atom, a hydroxyl group, a straight or branched alkoxy group having 1 to 6 carbon atoms, a straight or branched alkylthio group having 1 to 6 carbon atoms, a carboxyl group, a straight or branched alkoxycarbonyl group having 2 to 6 carbon atoms, an aryloxycarbonyl group having 7 to 13 carbon atoms, a cyano group, an amino group, an alkylamino group having 1 to 4 carbon atoms, a dialkylamino group having 2 to 8 carbon atoms, a cycloalkyl group having 3 to 7 carbon atoms, or an aromatic hydrocarbon group having not more than 10 carbon atoms; $X^1$ represents a carbonyl group or a methylene group; k represents 0 or an integer of 1 to 5, provided that when $X^1$ is a carbonyl group and $R^7$ is a hydroxyl group or when $X^1$ is a methylene group and $R^7$ is a hydroxyl group, an amino group, an alkylamino group or a dialkylamino group, k represents an integer of 1 to 5; and each of A and B independently represents a methylene group or a group shown by:

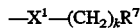

wherein each of $R^2$ and $R^3$ independently represents a hydrogen atom, an alkoxycarbonyl group, an unsubstituted alkyl group, or an alkyl group having 1 to 3 carbon atoms substituted with a hydroxy group, an amino group, an alkylamino group having 1 to 4 carbon atoms, or a dialkylamino group having 2 to 8 carbon atoms;

provided that when $R^1$ is a methyl group, A and B are not a methylene group simultaneously;

or a pharmaceutically acceptable salt.

11. A compound according to claim 10, wherein $R^1$ is a hydrogen atom, a straight or branched alkyl group having 1 to 6 carbon atoms, a straight or branched alkanoyl group having 1 to 6 carbon atoms, an aroyl group having not more than 11 carbon atoms, or a group shown by formula —$X^1$—$(CH_2)_k R^7$, wherein $R^7$, $X^1$ and k are as defined in claim 1, or a pharmaceutically acceptable salt thereof.

12. A compound according to claim 10, wherein $R^1$ is a hydrogen atom, a straight or branched alkanoyl group having 1 to 6 carbon atoms, an aroyl group having not more than 11 carbon atoms, or a group shown by formula —$X^1$—$(CH_2)_k R^7$, wherein $R^7$, $X^1$ and k are as defined in claim 1, or a pharmaceutically acceptable salt thereof.

13. A compound according to claim 11, wherein k is 0, 1 or 2, or a pharmaceutically acceptable salt thereof.

14. A compound according to claim 13, wherein $R^1$ is a hydrogen atom, a straight or branched alkyl group having 1 to 6 carbon atoms, a straight or branched alkanoyl group having 1 to 6 carbon atoms, an aroyl group having not more than 11 carbon atoms, or a group shown by formula —$X^1$—$(CH_2)_k R^7$;

wherein $R^7$ is a halogen atom, a hydroxyl group, a straight or branched alkoxy group having 1 to 6 carbon atoms, a straight or branched alkylthio group having 1 to 6 carbon atoms, a carboxyl group, a straight or branched alkoxycarbonyl group having 2 to 6 carbon atoms, an aryloxycarbonyl group having 7 to 13 carbon atoms, a cyano group, an alkylamino group having 1 to 4 carbon atoms, a dialkylamino group having 2 to 8 carbon atoms, a cycloalkyl group having 3 to 7 carbon atoms, or an aromatic hydrocarbon group having not more than 10 carbon atoms; and $X^1$ is a carbonyl group, or a pharmaceutically acceptable salt thereof.

15. A compound according to claim 13, wherein $R^1$ is a hydrogen atom, a straight or branched alkyl group having 1 to 6 carbon atoms, a straight or branched alkanoyl group having 1 to 6 carbon atoms, an aroyl group having not more than 11 carbon atoms, or a group shown by formula —$X^1$—$(CH_2)_k R^7$;

wherein $R^7$ is a halogen atom, a hydroxyl group, a straight or branched alkoxy group having 1 to 6 carbon atoms, a straight or branched alkylthio group having 1 to 6 carbon atoms, a carboxyl group, an aryloxycarbonyl group having 7 to 13 carbon atoms, an amino group, an alkylamino group having 1 to 4 carbon atoms, a dialkylamino group having 2 to 8 carbon atoms, or a cycloalkyl group having 3 to 7 carbon atoms; and $X^1$ is a methylene group, or a pharmaceutically acceptable salt thereof.

16. A compound according to claim 14, wherein A and B each represents a methylene group, or a pharmaceutically acceptable salt thereof.

17. A compound according to claim 15, wherein A and B each represents a methylene group, or a pharmaceutically acceptable salt thereof.

18. A compound represented by formula:

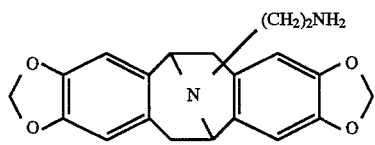

or a pharmaceutically acceptable salt thereof.

19. A pharmaceutical composition for inhibiting the production or secretion of a tumor necrosis factor, which comprises an effective amount for inhibiting the production or secretion of tumor necrosis factor of a compound of claim 18 or a pharmaceutically acceptable salt thereof and a pharmaceutically acceptable carrier or diluent.

20. A compound of the formula:

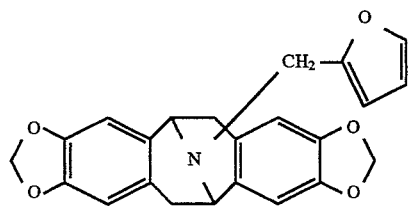

or a pharmaceutically acceptable salt thereof.

21. A compound of the formula:

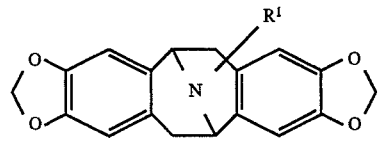

wherein $R^1$ represents the group shown below:

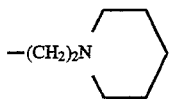

or a pharmaceutically acceptable salt thereof.

* * * * *